(12) United States Patent
Lapidot et al.

(10) Patent No.: US 7,160,992 B2
(45) Date of Patent: *Jan. 9, 2007

(54) AMINO-MODIFIED POLYSACCHARIDES AND METHODS OF GENERATING AND USING SAME

(75) Inventors: Aviva Lapidot, Rehovot (IL); Veerappan Vijayabaskar, Tamil Nadu (IN); Gadi Borkow, Kfar Gibton (IL)

(73) Assignee: Yeda Research and Development Co., Ltd., Rechovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/831,224

(22) Filed: Apr. 26, 2004

(65) Prior Publication Data

US 2004/0229265 A1 Nov. 18, 2004

Related U.S. Application Data

(60) Provisional application No. 60/465,775, filed on Apr. 28, 2003.

(51) Int. Cl.
*C07H 15/20* (2006.01)
*C07H 15/22* (2006.01)
*A61K 31/70* (2006.01)

(52) U.S. Cl. ............ 536/13.2; 536/13.3; 514/41; 514/42; 514/62

(58) Field of Classification Search ............ None
See application file for complete search history.

(56) References Cited

U.S. PATENT DOCUMENTS

2005/0085432 A1* 4/2005 Lapidot .................. 514/42

OTHER PUBLICATIONS

Aboul-Ela et al, "The structure of the human immunodeficiency virus type-I TAR RNA reveals principles of RNA recognition by Tat protein", *J MOl Biol*. Oct. 20, 1995;253(2):313-32.
Appelt k, "Crystal structures of HIV-1 protease-inhibitor complexes", *Pers in Drug Disc & Design*,, 1:23-48, 1993.
Baldwin et al, "Inhibiting HIV-1 entry with fusion inhibitors", *Curr Med Chem*. Sep. 2003;10(17):1633-42.
Bartel et al, "HIV-1 Rev regulation involves recognition of non-Watson-Crick base pairs in viral RNA", *Cell*. Nov. 1, 1991;6793):529-36.
Battiste et al, "Alpha helix-RNA major groove recognition in an HIV-1 rev peptide-RRE RNA complex", *Science*. Sep. 13, 1996;2763(5281):1547-51.
Berger et al, "Chemokine receptors as HIV-1 coreceptors: roles in viral entry, tropism, and disease", *Annu Rev Immunol*. 1999;17:657-700.
Borkow et al, "Chemical barriers to human immunodeficiency virus type 1 (HIV-1) infection: retrovirucidal activity of UC781, a thiocarboxanilide nonnucleoside inhibitor of HIV-1 reverse transcriptase", *J Virol*. Apr. 1997;71(4):3023-30.
Borkow et al, "Mutations in gp41 and gp120 of HIV-1 isolates resistant to hexa-arginine neomycin B conjugate", *Biochem Biophys Res Commun*. Dec. 26, 2003;312(4):1047-52.
Borkow et al, "Structure-activity relationship of neomycin, paromomycin, and neamine-arginine conjugates, targeting HIV-1 gp120-CXCR4 binding step", *Antiviral Res*. Nov. 2003;60(3):181-92.

(Continued)

*Primary Examiner*—Cecilia J. Tsang
*Assistant Examiner*—Andrew D. Kosar

(57) ABSTRACT

Novel amino-modified polysaccharides are provided. The amino-modified polysaccharides have one or more amino groups, each being linked to one or more arginine residues.

6 Claims, 14 Drawing Sheets
(3 of 14 Drawing Sheet(s) Filed in Color)

|  | $R_1$ | $R_2$ | $R_3$ | $R_4$ | $R_5$ | $R_7$ |
|---|---|---|---|---|---|---|
| Neomycin | NH2 | NH$_2$ | NH$_2$ | NH$_2$ | NH$_2$ | NH$_2$ |
| NeoR6 | Arg | Arg | Arg | Arg | Arg | Arg |
| NeoR1 | Arg | NH$_2$ | NH$_2$ | NH$_2$ | NH$_2$ | NH$_2$ |
| NeoR1 | NH$_2$ | NH$_2$ | NH$_2$ | NH$_2$ | NH$_2$ | Arg |
| NeoR2 | Arg | NH$_2$ | NH$_2$ | NH$_2$ | NH$_2$ | Arg |
| Neamine | NH$_2$ | NH$_2$ | NH$_2$ | NH$_2$ |  |  |
| NeamR1 | Arg | NH$_2$ | NH$_2$ | NH$_2$ | -- | -- |
| NeamR4 | Arg | Arg | Arg | Arg | -- | -- |
| Paromomycin | OH | NH$_2$ | NH$_2$ | NH$_2$ | NH$_2$ | NH$_2$ |
| ParomR1 | OH | NH2 | NH$_2$ | NH$_2$ | NH$_2$ | Arg |
| ParomR5 | OH | Arg | Arg | Arg | Arg | Arg |

| | $R_1$ | $R_2$ | $R_3$ |
|---|---|---|---|
| Gentamicin C1 R3G | NH$_2$ Arg | NH$_2$ Arg | NH$_2$ Arg |

OTHER PUBLICATIONS

Bradshaw et al, "Preparation of diamino ethers and polyamines", *Tetrahedron*, 48(22:4475-4515, 1992.

Le Bris, "One Pot Symentrical and Dissymentrical Regiospecific ω, ω$^1$-Bis Mono N-Alkylation of Linear Tetraamines via their Chromium, Molybdneum or Tungsten Tricarbonyl Complexes", Tetrahedron Letters, 34(34):5429-5432, 1993.

Brodsky rt al, "Solution structure of the HIV-2 TAR-argininamide complex", *J Mol Biol*. Apr. 4, 1997;267(3):624-39.

Cabrera et al, "Anti-human immunodeficiency virus activity of novel aminoglycoside-arginine conjugates at early stages of infection", *AIDS Res Hum Retroviruses*. May 1, 2000;16(7):627-34.

Cabrera et al, "Anti-HIV activity of a novel aminoglycoside-arginine conjugate", *Antiviral Res*. Jan. 2002;53(1):1-8.

Calnan et al, "Arginine-mediated RNA recognition: the arginine fork", *Science*. May 24, 1991;252(5010):1167-71. Erratum in: Science Feb. 7, 1992;255(5045):665.

Carriere et al, "Inhibition of protein synthesis by aminoglycoside-arginine conjugates", *RNA*. Oct. 2000;8(10);1267-79.

Catani et al, "The Tat antagonist neomycin B hexa-arginine conjugate inhibits gp-120-induced death of human neuroblastoma cells", *J Neurochem*. Mar. 2003;84(6):1237-45.

Chackerian et al, "Human immunodeficiency virus type 1 corecptors participate in postentry stages in the virus replication cycle and function in simian immunodeficiency virus infection",*J Virol*. May 1997;71(5):3932-9.

Chan et al, "Core structure of gp41 from the HIV envelope glycoprotein", Cell. Apr. 18, 1997;89(2):263-73.

Chapman et al, "Small molecule modulators of HIV Rev/Rev response element interaction identified by random screening", *Antiviral Res*. Jun. 2002;54(3):149-62.

Chatterjee et al, "Dual-target inhibition of HIV-1 in vitro by means of an adeno-associated virus antisense vector", *Science*. Nov. 27, 1992;258(5087):1485-8.

Cheng et al, "Design of RNA-binding proteins and ligands", *Curr Opin Struct Biol*. Aug. 2001;11(4):478-84.

Choe et al, "Structural interactions between chemokine receptors, gp120 Env and CD4", *Semin Immunol*. Jun. 1998;10(3):249-57.

Clapham et al, "HIV-1 receptoras and cell tropism", *Br Med Bull*. 2001;58:43-59.

Collins et al, "Development of an in vitro organ model to study transmission of HIV-1 in the female gential tract", *Nat Med*. Apr. 2000;6(4):475-9.

De Clercq, E., "New anti-HIV agents and targets", *Med Res Rev*. Nov. 2002;22(6):531-65.

De Vreese et al, "The molecular target of bicyclams, potent inhibitors of human immunodeficiency virus replication", *J Virol*. Feb. 1996;70(2):689-96.

Delling et al, "The number of positively charged amino acids in the basic domain of Tat is critical for trans-activation and complex formation with TAR RNA", *Proc Natl Acad Sci U S A*. Jul. 15, 1991;88(14):6234-8.

Erikson, JW, "Design and structure of symmetry-based inhibitors of HIV-1 protease", *Perspective in Drug Discovery and Design*, 1:109-128, 1993.

Enninfar et al, "HIV-1 RNA dimerization initiation site is structurally similar to the ribosmal A site and binds aminoglycoside antibiotics", *J Biol Chem*. Jan. 24, 2003;278(4):2723-30. Epub Nov. 14, 2002.

Este, JA, "Virus entry as a target for anti-HIV intervention", *Curr Med Chem*. Sep. 2003;10(17):1617-32.

Eubank et al, "Inhibition of bacterial RNase P by aminoglycoside-arginine conjugates" *FEBS Lett*. Jan. 30, 2002;511(1-3):107-12.

Fourmy et al, "Binding of neomycin-class aminoglycoside antibiotics to the A-site of 16 S rRNA", *J Mol Biol*. Mar. 27, 1998;277(2):347-62.

Gohlke et al, "Statistical potentials and scoring functions applied to protein0ligand binding", *Curr Opin Struct Biol*. Apr. 2001;11(2):231-5.

Gosser et al, "Peptide-triggered conformational switch in HIV-1 RRE RNA complexes", *Nat Struct Biol*. Feb. 2001;8(2):146-50.

Halperin et al, "Principles of docking: An overview of search algorithms and a guide to scoring functions", *Proteins*. Jun. 1, 2002;47(4):409-43.

Hamasaki et al, "Aminoglycoside antibiotics, neamine and its derivatives as potent inhibitors for the RNA-protein interactions derived from HIV-1 activators", *Bioorg Med Chem Lett*. Feb. 26, 2001;11(4):591-4.

Hung et al, "The crystal structure of the Rev binding element of HIV-1 reveals novel base pairing and conformational variability", *Proc Natl Acad Sci U S A*. May 9, 2000;97(10):5107-12.

Ippolito et al, "The structure of the HIV-1 RRE high affinity rev binding site at 1.6 A resolution", *J Mol Biol*. Jan. 28, 2000;295(4):711-7.

Kjems et al, "Specific binding of a basic peptide from HIV-1 Rev", *EMBO J*. Mar. 1992;11(3):1119-29.

Krakowiak et al, "Selective Protection of the Primary Amine Functions of Linear Teraamines Usinf the Trityl Group", *Synthetic Comm.*, 28(18):3451-3459, 1998.

Lacourciere et al, "Mechanism of neomycin and Rev peptide binding to the Rev responsive element of HIV-1 as determined by fluorescence and NMR spectroscopy", *Biochemistry*. May 16, 2000;39(19):5630-41.

Lam et al, "Rational design of potent, bioavailable , nonpeptide cyclic ureas as HIV protease inhibitors", *Science*. Jan. 21, 1994;263(5145):380-4.

Lapidot et al, "Novel HIV Tat antagonists", *Drug Development Research* 50:502-515, 2000.

Litovchick et al, "Aminoglycoside-arginine conjugates that bind TAR RNA: synthesis, characterization, and antiviral activity", *Biochemistry*. Mar. 21, 2000;39(11)2838-52.

Litovchick et al, "Neomycin B-arginine conjugate, a novel HIV-1 Tat antagonist: synthesis and anti-HIV activities", *Biochemistry*. Dec. 25, 2001;40(51):15612-23.

Litovchick et al, "Arginine-aminoglycoside conjugates that bind to HIV transactivation responsive element RNA in vitro", *FEBS Lett*. Feb 19, 1999;445(1):73-9.

Long et al, "Charcterization of the solution conformations of unbound and Tat peptide-bound forms of IV-1 TAR RNA", *Biochemistry*. Aug. 3, 1999;38(31):10059-69.

Lu et al, "Detrytilation with ytterbium triflate", *Tetrahedron Lett*., 41:2817-2819, 2000.

Ma et al, "Impaired B-lymphopoiesis, myelopoiesis, and derailed cerebellar neuron migration in CXCR4- and SDF-1-deficient mice", *Proc Natl Acad Sci U S A*. Aug. 4, 1998;95(16):9448-53.

Martin, YC, "3D database searching in drug design", *J Med Chem*. Jun. 12, 1992;35(12):2145-54. Review.

Mauro et al, "STI571: a paradigm of new agents for cancer therapeutics", *J Clin Oncol*. Jan. 1, 2002;20(1):325-34.

Mei et al, "Inhibition of an HIV-1 TAT-Derived Peptide Binding to TAR RNA by Aminoglycoside Antibiotics", *Boorg. & Med. Chem.*, 5(22):2755-2760, 1995.

Mayers, DL, "Prevalence and incidende of resistance to zidovudine and other antiretroviral drugs", *Am J Med*. May 19, 1997;102(5B):70-5.

Michael et al, "HIV-1 entry inhibitors: evading the issue", *Nat Med*. Jul. 1999;5(7):740-2.

Mohle et al, "Regulation of transendothelial migration of hematopoietic progenitor cells", *Ann N Y Acad Sci*. Apr. 30, 1999;872:176-85.

Mondor et al, "Interactions among HIV gp120, CD4, and CXCR4: dependence on CD4 expression level, gp12 viral origin, conservation of the gp120 COOH- and NH2-termini and V1/V2 and V3 loops, and sensitivity to neutralizing antibodies", *Virology*. Sep. 1, 1998;248(2):394-405.

Moore et al, "New targets for inhibitors of HIV-1 replication", *Nat Rev Mol Cell Biol*. Oct. 2000;1(1):40-9.

Moore et al, "The entry of entry inhibitors: a fusion of science and medicine", *Proc Natl Acad Sci U S A*. Sep. 16, 2003;100(19):10598-602. Epub Sep 5, 2003.

Nagasawa et al, "Defects of B-cell ly,phopoisis and bone-marrow myelopoiesis in mice lacking the CXC chemokine PBSF/SDF-1", *Nature*. Aug. 15, 1996;382(6592):635-8.

Noller, HF, "ribosomal RNA and translation", *Annu Rev Biochem.* 1991;60:191-227.

O'hara et al, "HIV entry inhibitors in clinical development", *Curr Opin Pharmacol.* Oct. 2002;2(5):523-8.

Ojwang et al, "Inhibition of human immunodeficiency virus type 1 expression by a hairpin ribozyme", *Proc Natl Acad Sci U S A.* Nov. 15, 1992;89(22):10802-6.

Park et al, "Rapid Combinatorial Synthesis of Aminoglycoside Antibiotic Mimetics: Use of a Polyethylene Glycol-Linked Amine and a Neamine-Derived Aldehyde in Multiple Component Condensation as a Strategy for the Discovery of New Inhibitors of the HIV RNA Rev Responsive Element", *J. Am. Chem. Soc.*; 1996; 118(42);10150-10155.

Perbal, B., "A Practical Guide to Molecular Cloning", John Wiley & Son, NY, 1988, pp. 30-42.

Pearson et al, "RNA as a Drug Target", Chem Biol, 4:409-414, 1997.

Peterson et al, "Structural change in Rev responsive element RNA of HIV-1 on binding Rev peptide", *J MOL Biol.* Dec. 20, 1996;264(5):863-77.

Rizzuto et al, "A conserved HIV gp120 glycoprotein structure involved in chemokine receptor binding", *Science.* Jun. 19, 1998;280(5371):1949-53.

Ryu et al, "Stereospecificity of aminoglycoside-ribosomal interactions", *Biochemistry.* Aug. 20, 2002;41(33):10499-509.

Schols et al, "T-cell-line-tropic human immunodeficiency virus type 1 that is made resistant to stromal cell-derived factor 1alpha contains mutations in the envelope gp120 but does not show a switch in coreceptor use", *J Virol.* May 1998;72(5):4032-7.

Spivey et al, "Synthetic Methods Part (iii) Protecitng Groups", *Annu Rep Prog Chem Sect B*, 98:41-60, 2002.

Staudinger et al, "HIV-1 envelope is a neutral antagonist to CXCR4 in T-cells", *Biochem Biophys Res Commun.* Feb. 2, 2001;280(4):1003-7.

Sullenger et al, "Overexpression of Tar sequences renders cells resistant to human immunodeficiency virus replication", *Cell.* Nov. 2, 1990;63(3):601-8.

Tok et al, "Binding of dimeric aminoglycosides to the HIV-1 rev responsive element (RRE) RNA construct", *Bioorg Med Chem Lett.* May 7, 2001;11(9):1127-31.

Trkola et al, "CD4-dependent, antibody-sensitive interactions between HIV-1 and its co-receptor CCR-5", *Nature.* Nov. 14, 1996;384(6605):184-7.

Ugolini et al, "HIV-1 gp120 induces an association between CD4 and the chemokine receptor CXCR4", *J Immunol.* Sep. 15, 1997;159(6):3000-8.

Wang et al, "Specificity of aminoglycoside binding to RNA constructs derived from the 16S rRNA decoding region and the HIV-RRE activator region", *Biochemistry*, Jan. 28, 1997;36(4):768-79.

Weeks et al, "Fragments of the HIV-1 Tat protein specifically bind TAR RNA", *Science.* Sep. 14, 1990;249(4974):1281-5.

Weissenhorn etal, "Atomic structure of the ectodomain from HIV-1 gp41", *Nature.* May 22, 1997;387(6631):426-30.

Wlodawer et al, "Structure-based inhibitors of HIV-1 protease", Annu Rev Biochem. 1993;62:543-85.

Wu et al, "CD4-induced interaction of primary HIV-1 gp120 glycoproteins with the chemokine receptor CCR-5", Nature. Nov. 14, 1996;384(6605):179-83.

Zaitseva et al, "HIV coreceptors: role of structure, posttranslational modifications, and internalization in viral-cell fusion and as target for entry inhibitors", *Biochim Biophys Acta.* Jul. 11, 2003;1614(1):51-61.

Zapp et al, "Small molecules that selectively block RNA binding of HIV-1 Rev protein inhibit Rev function and viral production", *Cell.* Sep. 24, 1993;74(6):969-78.

Zeng, J., "Mini-review: computational structure-based design of inhibitors that target protein surfaces", *Comb Chem High Throughput Screen.* Oct. 2000;3(5):355-62.

Zhang et al, "Structural characterization of the complex of the Rev response element RNA with a selected peptide", *Chem Biol.* May 2001;8(5):511-20.

Zou et al, "Function of the chemokine receptor CXCR4 in haematopoiesis and in cerebellar development", *Nature.* Jun. 11, 1998;393(6685):595-9.

\* cited by examiner

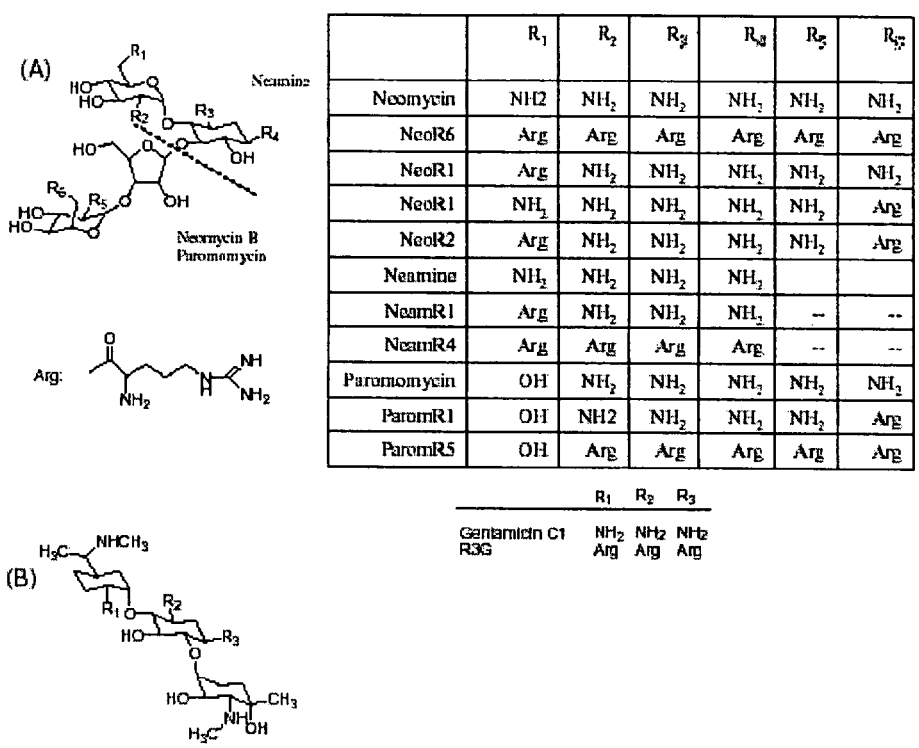
Figures 2a-b

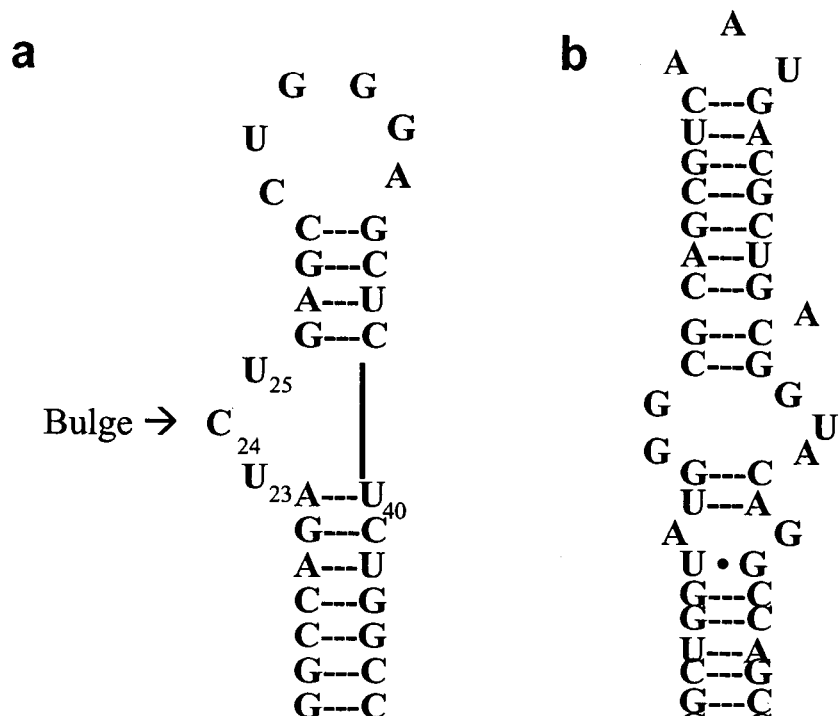
TAR RNA
(SEQ ID NO: 19)
RRE IIB RNA
(SEQ ID NO: 20)
c
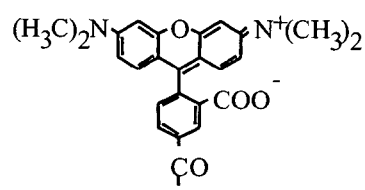
RhdRev
TRQARRNNRRRRWRERQR
(SEQ ID NO: 21)
Figures 3a-c

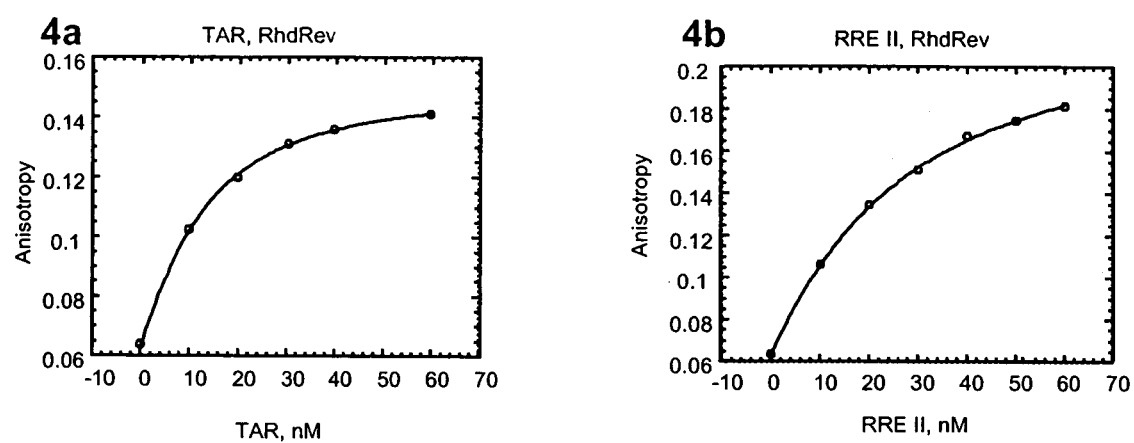
Figures 4a-b

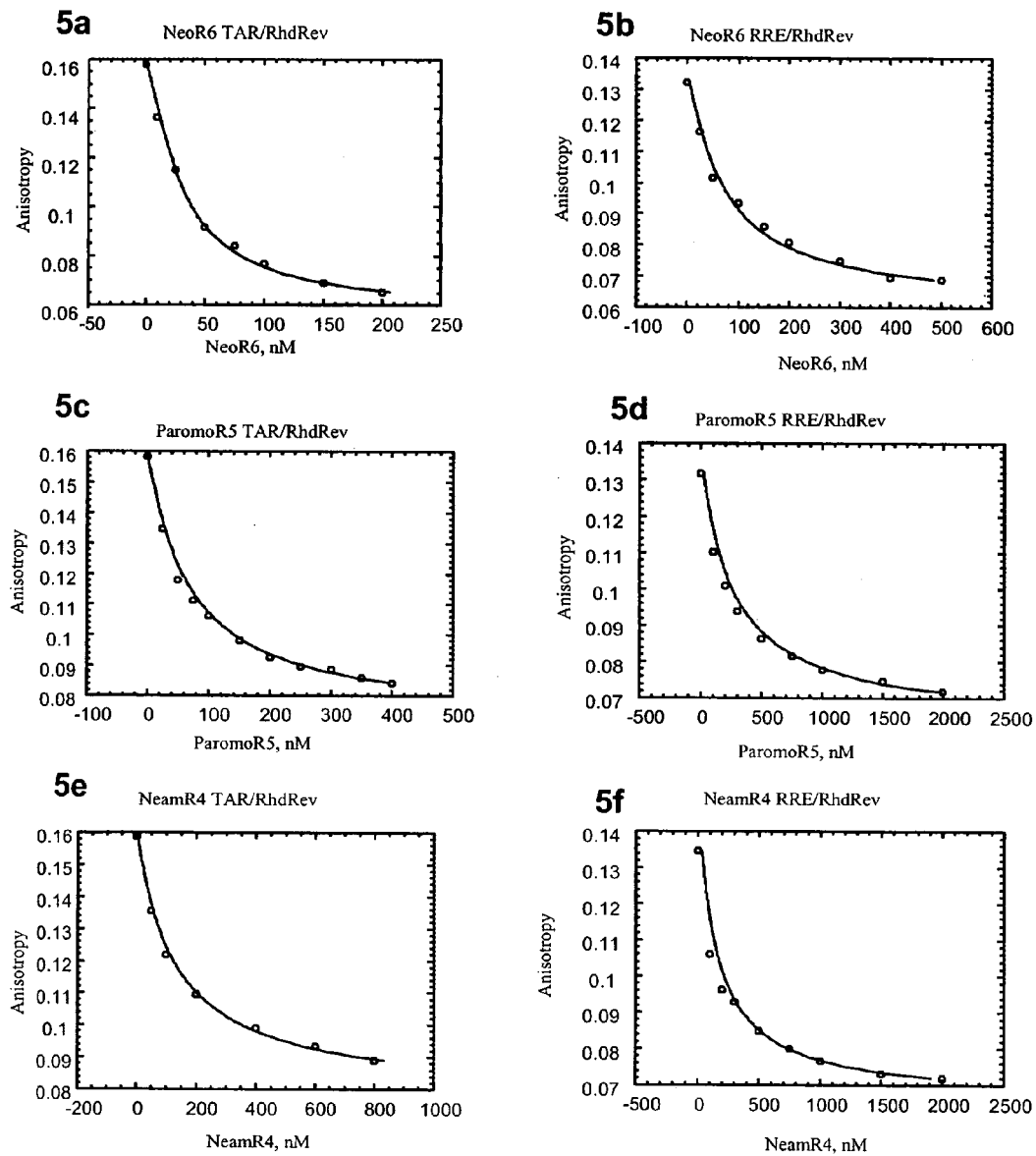
Figures 5a-f

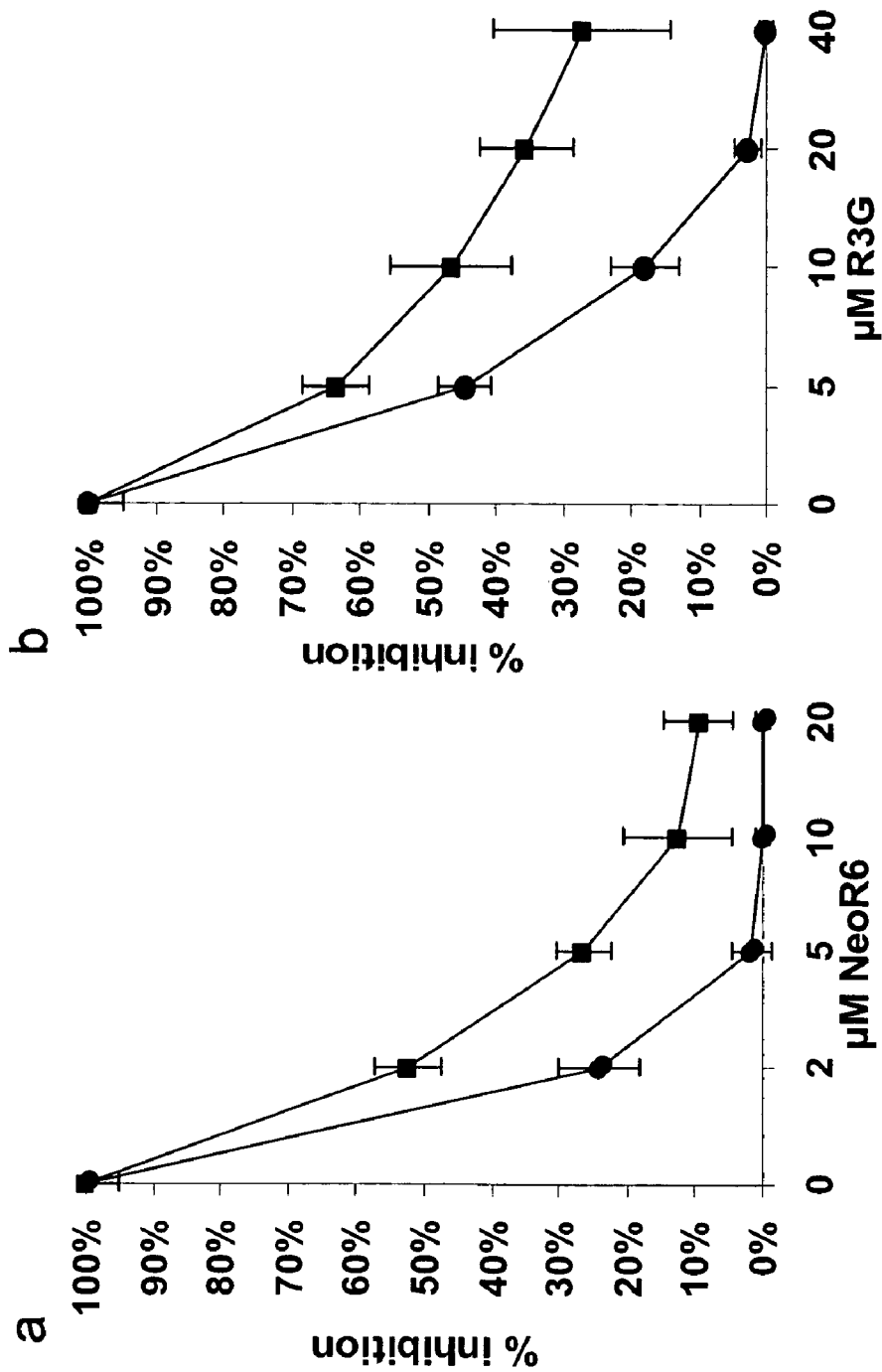
Figures 7a-b

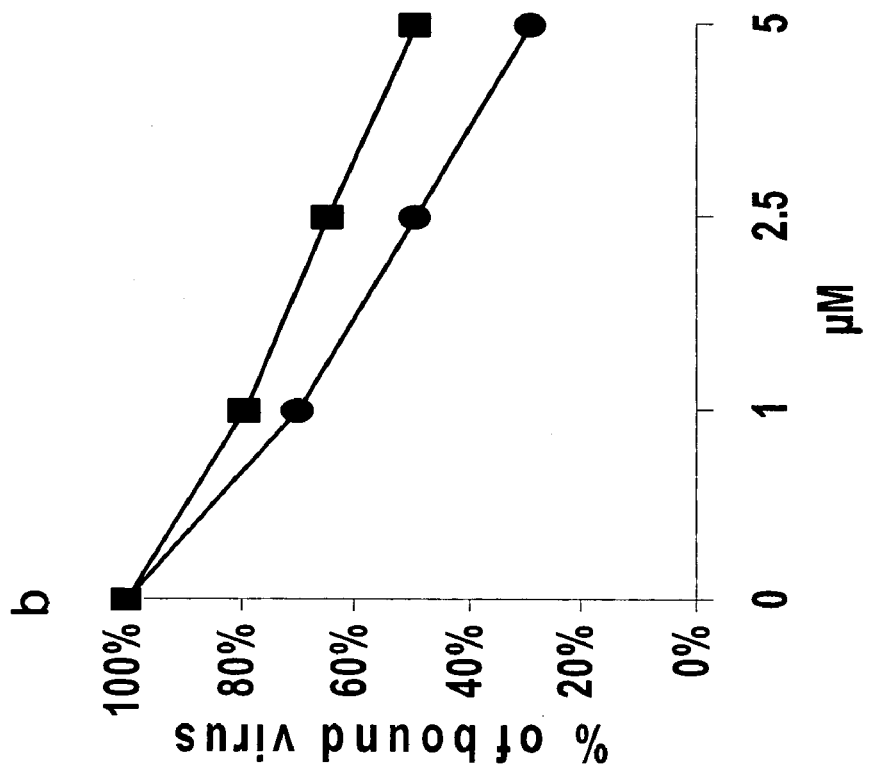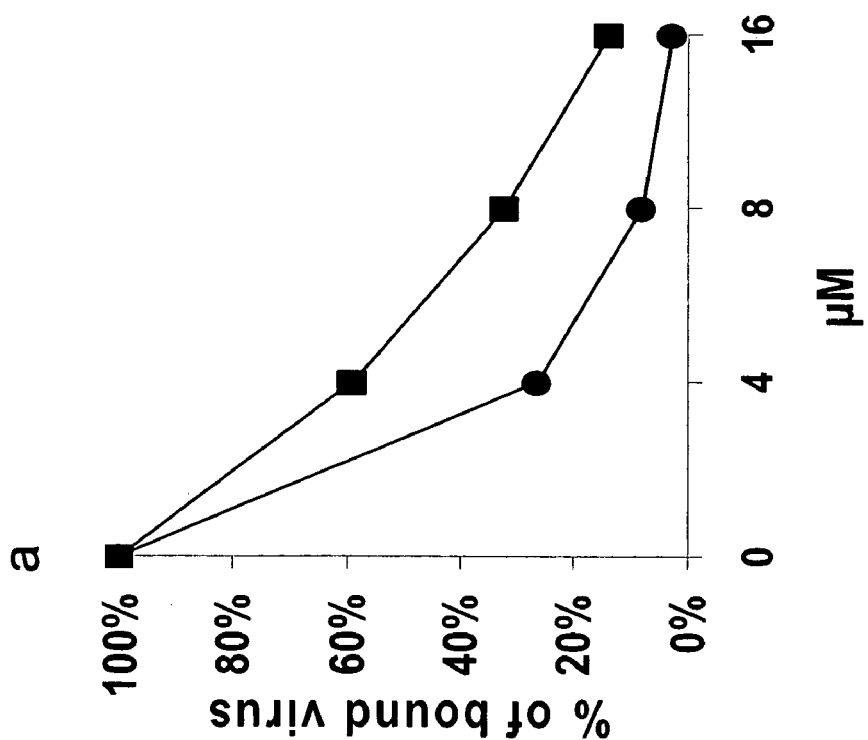
Figures 8a-b

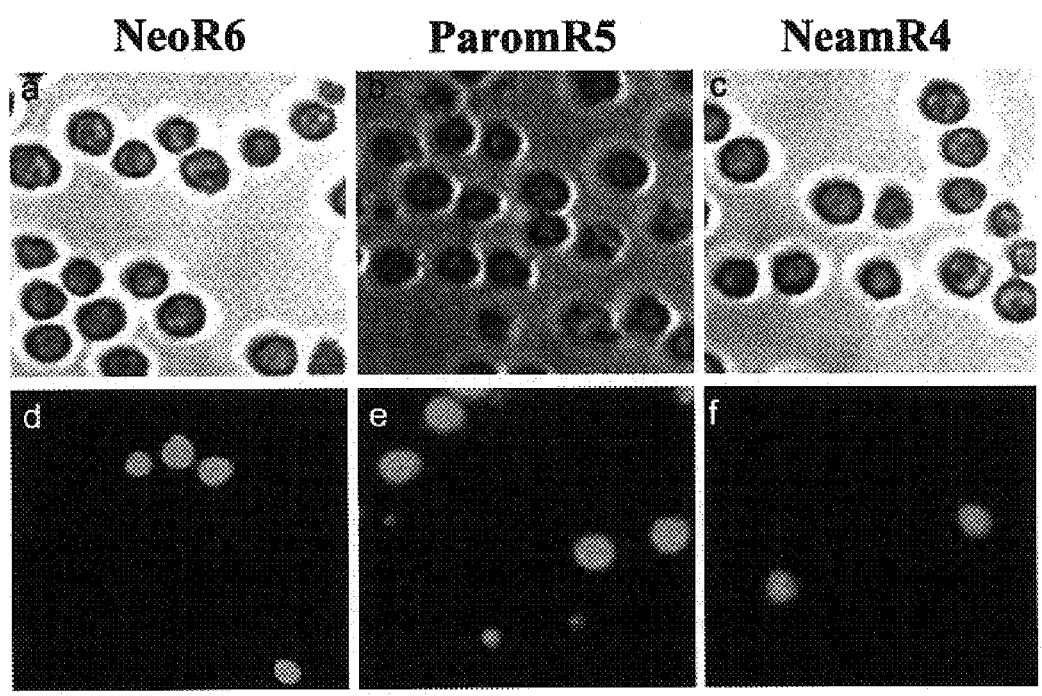
Figures 9a-f

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 1
ttctcgcttg tactgggtct c                                              21

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
cgttttcaag tccctgttcg                                                20

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
tggaaaatct ctagcagtgg c                                              21

<210> SEQ ID NO 4
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 4 tttttcttt cccctgg                                                    18
```

<210> SEQ ID NO 5
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 5
cgacatagca gaataggcgt t        21

<210> SEQ ID NO 6
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 6
tccttcactc tcattgccac t        21

<210> SEQ ID NO 7
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 7
agtgttgctt tcattgccaa g        21

<210> SEQ ID NO 8
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 8
tcaacatccc aaggagcat        19

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
tgttaaatgg cagcctagca        20

<210> SEQ ID NO 10
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 10
cacttctcca attgtccctc a        21

<210> SEQ ID NO 11
<211> LENGTH: 22
<212> TYPE: DNA
<213> ORGANISM: Artificial sequence
<220> FEATURE:
<223> OTHER INFORMATION: Single strand DNA oligonucleotide -continued

```
<400> SEQUENCE: 11
cagaacaatt tgctgagggc ta                                              22

<210> SEQ ID NO 12
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 12
ccacccatct tatagcaaaa tcc                                             23

<210> SEQ ID NO 13
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 13
gagaaaaaag agcagtggga a                                               21

<210> SEQ ID NO 14
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 14
cagagcaacc ttaaatccca a                                               21

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
aggcagggat attcaccatt                                                 20

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16
agtaagtctc tcaagcggtg g                                               21

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
ccattatcgt ttcagaccca                                                 20

<210> SEQ ID NO 18
<211> LENGTH: 21
```

-continued

```
<212> TYPE: DNA
<213> ORGANISM: Artificial sequence
<220> FEATURE:
<223> OTHER INFORMATION: Single strand DNA oligonucleotide

<400> SEQUENCE: 18
ccaagccctg tcttattctt c                                              21
```

AMINO-MODIFIED POLYSACCHARIDES AND METHODS OF GENERATING AND USING SAME

This application claims the benefit of priority from U.S. Provisional Patent Application No. 60/465,775, filed 28 Apr. 2003, the content thereof is hereby incorporated by reference.

FIELD AND BACKGROUND OF THE INVENTION

The present invention relates to amino-modified polysaccharides and more particularly, to methods of generating and using the same, such as in treating viral infections such as AIDS.

HIV is the causative agent of acquired immunodeficiency syndrome (AIDS), a fatal human disease, which has affected numerous individuals worldwide. A vast amount of research is currently being undertaken to find new therapies and new drugs, which may provide some assistance in combating the HIV virus. One approach for drug therapy is to target viral proteins in an attempt to inhibit or halt viral replication. Presently, a triple-drug "cocktail" therapy regimen is the most effective approach to controlling the AIDS virus. This "cocktail" therapy includes a combination of a protease inhibitor called indinavir™ with two reverse-transcriptase inhibitors known as AZT™ and 3TC™. The triple drug therapy results in a decrease in measured levels of virus in both blood and lymphatic tissues. However, a proportion of those treated, whose viruses had developed resistance to one or more of the cocktail's reverse-transcriptase inhibitors as a result of previous treatment, fail to respond. Some studies have projected that the combination therapy can virtually eliminate the AIDS virus within two or three years from those patients who respond to treatment. However, other studies indicate that minimal residual virus is sufficient to cause relapse. In addition, current pharmacologic therapies leave residual HIV genes lurking in cells in the form of latent "provirus." As long as the cells remain alive, these genes can be transcribed, facilitating virus production. For these reasons, currently available drug therapy must be maintained throughout patient's life, resulting in long term adverse side effects and treatment costs of over $15,000 annually for each patient.

Thus, there is a continuing need to develop additional approaches to controlling HIV infection which can be used alone or in combination with existing therapies.

The process of HIV-1 viral infection involves the interaction of the gp120 Env protein with the CD4 receptor and the CXCR4 and CCR5 chemokine coreceptors on the target cell (reviewed in Berger, E. A. et al., 1999. Annu. Rev. Immunol. 17: 657–700; Cammack, N. 1999. Antivir. Chem. Chemother. 10: 53–62; Choe, H. et al., 1998. Semin. Immunol 10: 249–257; Clapham and McKnight 2001. Br. Med. Bull. 58: 43–59; Zaitseva, M. et al., 2003. Biochim. Biophys. Acta 1614: 51–61). These interactions form a trimolecular complex (gp120-CD4-chemokine receptor) which stabilizes virus binding and triggers a series of conformational changes in the second Env protein, gp41. These conformational changes lead to lipid mixing and fusion of the cellular and viral membranes, which result in entering of the viral core into the cell (reviewed in J. P. Moore and R. W. Doms, 2003. Proc. Natl. Acad. Sci. U.S.A 100: 10598–10602).

The discovery of virus entry and the consequent understanding the receptor-induced conformational changes in the Env protein and virus-cell fusion, led to the development of entry inhibitors [J. P. Moore and M. Stevenson, 2000. Nat. Rev. Mol. Cell Biol. 1: 40–49; B. M. O'Hara and W. C. Olson, 2002. Curr. Opin. Pharmacol. 2: 523–528]. The overall viral entry process (binding and fusion) can be blocked by a number of compounds. These include siamycin analogues, SPC 3 (a synthetic peptide derived from the V3 domain of gp120), pentafuside (T20, DP178, a synthetic peptide corresponding to amino acid residues 127 to 162 of gp41), the betulinic acid derivative RPR 103611, TAK 779 (a low molecular weight non-peptide CCR5 antagonist) and a number of compounds (T22, T134, ALX40-4C, CGP64222 and AMD 3100) that target the CXCR4 coreceptor (reviewed in Zaitseva, M. et al., 2003. Biochim. Biophys. Acta 1614: 51–61; De Clercq, E. 2002. Med. Res. Rev. 22: 531–565; De Clercq, E. 1999. Drugs R.D. 2: 321–331; Este, J. A. 2003. Curr. Med. Chem. 10: 1617–1632; Baldwin, C. E. et al., 2003. Curr. Med. Chem. 10: 1633–1642). One of these entry inhibitors, T20 (Trimeris, Durham, N.C.), has been approved for clinical use (M. L. Duffalo and C. W. James, 2003. Enfuvirtide: A Novel Agent for the Treatment of HIV-1 Infection. Ann. Pharmacother. 37:1448–1456). However, since the entry inhibitors are targeted against the viral Env protein, which is the most variable protein among primary HIV-1 viruses, the various HIV-1 strains have different sensitivity towards the entry inhibitors. In fact, the extent of strain-to-strain variation is markedly greater for entry inhibitors than it is for reverse transcriptase and protease inhibitors [Moore and Doms (Supra)].

Recently, RNA has been recognized as a target site for therapeutic intervention because of its central role in protein synthesis [Pearson and Prescott (1997) Chem. Biol. 4:409–14]. The advantages of targeting RNA over traditional protein targets include the slower development of drug resistance against small molecules, the high conservation of RNA functional domains and accessibility of RNA functional domains to drugs. The HIV virus, which has rapidly developed resistance to enzyme inhibitors, has thus become an important target for RNA-targeted small molecules. The trans activating region (TAR) RNA and the Rev responsive element both responsible for gene regulation in HIV, have been identified as possible RNA-based targets. The RNA functional domain of TAR binds the cognate peptide Tat, which activates transcription of the HIV genome.

HIV-1 specific ribozymes, antisense RNA, and RNA decoys have also been proposed as potential therapeutic reagents for HIV-1 [Chatterjee, S., et al., Science 258, 1485–1488 (1992); Sullenger, B. A., et al., Cell 63, 601–608 (1990); Ojwang, J. O., et al., PNAS 89, 10802–10806 (1992)]. Some examples are provided in WO92/05195 which discloses molecules that mimic the high-affinity binding site of the native RRE in order to act as competitive inhibitors, thus sequestering free Rev protein and preventing it from interacting with those mRNAs which contain the RRE. These molecules contain a greater number of Rev binding sites than are contained in viral RRE-containing mRNAs.

Additionally, Jensen and co-workers (1995) disclose chemically modified RNA sequences (i.e., containing 5-iodouridine) which bind Rev in vitro with higher affinity than the RRE and which are able to crosslink with Rev at a 1:1 ratio. These are postulated as potential suicide ligands for in vivo disease inhibition, however, non-specific interactions with chemically reactive bases cannot be ruled out under in vivo conditions.

Aminoglycosides have found clinical use as antibacterial agents, owing to their ability to bind 16S RNA of 30S subunit of bacterial ribosomes, which could alter the function of the target RNA [Noller (1991) Annu. Rev. Biochem. 60:191–227]. Aminoglycosides were also shown to interact with a large number of other RNAs including the two essential elements of the HIV genome, the Rev responsive element (RRE) and the transactivation responsive element [(TAR); Zapp (1993) Cell 74:969–978; Mei (1995) Bioorg. Med. Chem. Lett. 5:25755–2760]. For example, the ability of neomycin B to bind at the minor groove of HIV TAR RNA leading to conformational changes in TAR, thus restricting Tat binding to the major groove of TAR-RNA has been independently exhibited by Faber (2000) J. Biol. Chem. 275:20660–6, and Puglisi (1993) Proc. Natl. Acad. USA 90:3680–3684.

NMR studies addressing aminoglycoside antibiotic binding to RNA suggest that rings I and II of the neomycin-class aminoglycosides are sufficient for mediating the specific interaction with the RNA [Fourmy (1998) J. Mol. Biol. 277:347–362]. However, additional rings and amino groups in this class of antibiotics increase RNA binding affinity [Ryu (2002) Biochemistry 41:10499–509].

Arginine- and lysine-rich basic peptides include a common motif of RNA recognition by proteins. Thus, for example, HIV Tat and Rev proteins mediate their interactions with the viral RNAs via an arginine-rich motif [Weeks (1990) Science 249:1281–1285]. Although the dominant contributions of the arginine side-chains may differ between complexes, the ability of the guanidinium groups of the arginine side chains to be involved in the electrostatic interactions, hydrogen bond formation, π—π and stacking interactions make arginine an important moiety for RNA recognition [Cheng (2001) Curr. Opin. Struct. Biol. 11:478–484].

Attempts to mimic the arginine-rich peptides led to the development of novel RNA ligands, which utilize a diverse set of building blocks [Litovchick (1999) FEBS Lett. 445: 73–79; Litovchik et al. (2000) Biochemistry 39: 2838–2852]. Arginine-rich RNA-binding peptides and peptidomimetics have provided a good scaffold for RNA-targeted drug design since they are short, conformationally diverse and contact RNA with high affinity and specificity.

The present inventors have recently designed and synthesized aminoglycoside-arginine conjugates (AACs) as potential anti-HIV-1 agents that combine the RNA binding ability of aminoglycosides and the specific binding of arginine moiety to HIV-1 TAR RNA (WO00/39139). AACs are designed to bind HIV TAR RNA and to inhibit transactivation by Tat protein. AACs are antagonists of the HIV-1 Tat protein basic domain and structurally are peptidomimetic compounds with different aminoglycoside cores and different numbers of arginines [Litovchick (1999) Supra.; Lapidot (2000) Drug Dev. Res. 50:502–515]. Along with inhibition of Tat trans-activation step in HIV life cycle, AACs exert a number of other activities, closely related to Tat antagonism. For example, hexa arginine neomycin B conjugate (NeoR6) inhibits the several functions of extra cellular Tat protein including upregulation of the HIV-1 viral entry co-receptor (CXCR4), increase of viral production, suppression of CD3-induced proliferation of lymphocytes, and upregulation of CD8 rereptor [Litovchick (2001) Biochemistry 40:15612–15623]. It was recently shown that NeoR6 and tri-arginine gentamicyn conjugate (R3G) inhibit binding of HIV particles to cells, probably by blocking the CXCR4 co-receptor [Litovchick (2000) Biochemistry 39:2838–2852; Litovchick (2001) Supra]. This was further substantiated by the finding that NeoR6 competes with the binding of the monoclonal antibody 12G5 to CXCR4, and CXCR4-SDF-1α binding [Litovchick (2001) Supra] and inhibits elevation of intracellular $Ca^{2+}$ induced by SDF-1α [Cabrera (2002) Antiviral Res. 53:1–8; Cabrera (2000) AIDS Res. Hum. Retroviruses 16:627–634]. Noteworthy is that AACs penetrate a variety of mammalian cells, including neurons and accumulate intracellularly [Litovchick (2001) Supra; and Litovchick (1999) Supra]. In particular, NeoR6 was shown to cross the blood brain barrier when administered systematically thereby penetrating various brain tissues (Catani, M. V. et al., 2003. J Neurochem. 84: 1237–45). All these render AACs multifunctional HIV Tat antagonists and therefore are highly important novel class of anti viral drugs.

The present inventors also found that AACs (e.g., NeoR6 and R3G) are able to elicit inhibition of bacterial RNAse P (Eubank T D, et al., 2002. Inhibition of bacterial RNase P by aminoglycoside-arginine conjugates. FEBS Lett. 511: 107–12) and to a lesser extent, mammalian RNAse P, which inhibition is far more significant than the inhibition elicited by their unconjugated aminoglycoside counterparts. Recently the capacity of several AACs to inhibit translation has also been presented [Carriere (2002) RNA 8:1267–1279].

In view of the ever-expanding roles of AACs in antibacterial and antiviral therapies, it is highly desirable to further elucidate the structural functional relationship of AAC binding to RNA and proteins, in order to design and identify anti viral drugs with improved therapeutic efficacy and reduced cytotoxicity.

While reducing the present invention to practice the present inventors have uncovered a new approach which allows for the synthesis of novel AACs with improved anti-bacterial and anti-viral activities.

SUMMARY OF THE INVENTION

According to one aspect of the present invention there is provided a pharmaceutical composition comprising, as an active ingredient, an amino-modified polysaccharide having at least one amino group linked to a peptide composed of at least two basic amino acid residues.

According to another aspect of the present invention there is provided a pentaargininamido-paromomycin conjugate (ParomR5).

According to yet another aspect of the present invention there is provided an argininamido-paramomycin conjugate (ParomR1) of a formula:

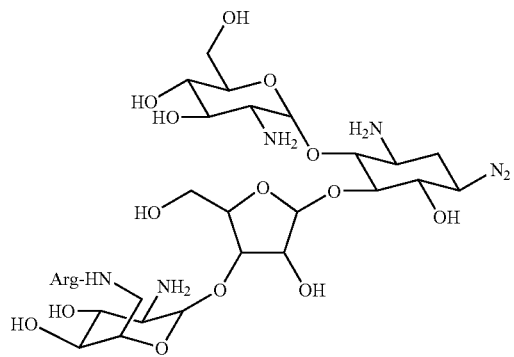

According to still another aspect of the present invention there is provided a tetraargininamido-neamine conjugate.

According to an additional aspect of the present invention there is provided an argininamido-neamine conjugate (NeamR1) of a formula:

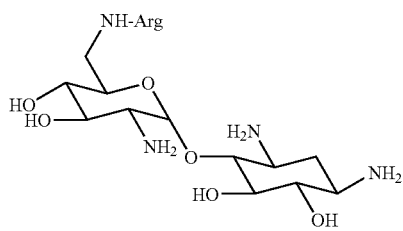

According to yet an additional aspect of the present invention there is provided a diargininamido-neomycin B conjugate (NeoR2) of a formula:

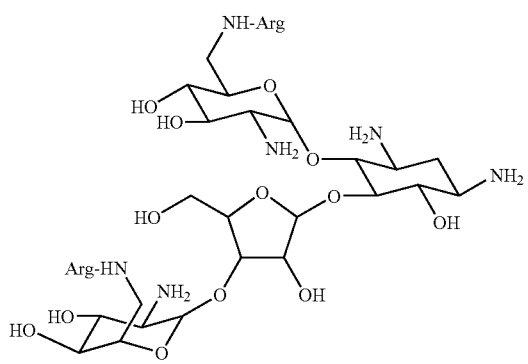

According to still an additional aspect of the present invention there is provided an argininamido-neomycin B conjugate (NeoR1) of a formula:

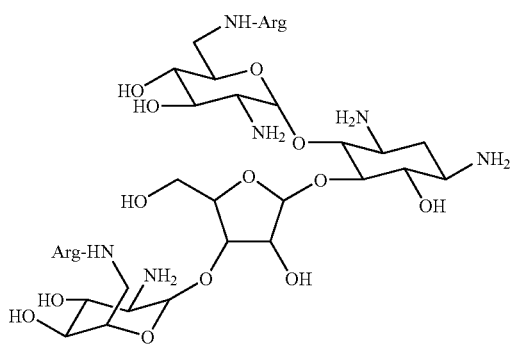

According to a further aspect of the present invention there is provided an argininamido-neomycin B conjugate (NeoR1) of a formula:

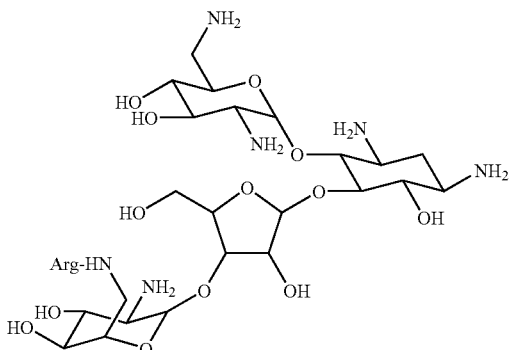

According to yet a further aspect of the present invention there is provided a method of selectively protecting an alkyl amino group of a polyamino cyclic compound, the method comprising attaching an N-protecting group to the alkyl amino group of the polyamino cyclic compound, the N—protecting group having a size selected suitable for selectively reacting with the alkyl amino group, to thereby selectively protect the alkyl amino group of the polyamino cyclic compound.

According to further features in preferred embodiments of the invention described below, the method further comprising protecting non-amine reactive groups of the polyamino cyclic compounds prior to the attaching the N-protecting group.

According to still further features in the described preferred embodiments the N-protecting group is a trityl halide.

According to still further features in the described preferred embodiments the trytil halide is trityl chloride.

According to still a further aspect of the present invention there is provided a method of generating a saccharide-chemical moeity site specific conjugate, the method comprising: (a) providing a saccharide having a reactive alkyl amino group and protected non-alkyl amino reactive groups; and (b) reacting the saccharide with a chemical moiety, thereby generating the saccharide-chemical moeity site specific conjugate.

According to still further features in the described preferred embodiments the saccharide is a mono-saccharide or an oligo-saccharide.

According to still further features in the described preferred embodiments the saccharide is an aminoglycoside antibiotic selected from the group consisting of neomycin, kanamycin, sisomycin, fortimycin, paromomycin, neamine and gentamycin.

According to still further features in the described preferred embodiments the moiety is an amino acid.

According to still further features in the described preferred embodiments the moiety is a cross linker.

According to still a further aspect of the present invention there is provided a method of identifying a potent anti HIV agent, the method comprising: (a) providing a plurality of putative anti HIV agents; and (b) identifying an anti HIV agent of the plurality of putative anti HIV agents incapable of inducing mutational instability in a predetermined sequence region of gp120, gp41, and/or CXCR4 thereby identifying the potent anti HIV agent.

According to still further features in the described preferred embodiments the sequence region is a nucleic acid sequence.

According to still further features in the described preferred embodiments the sequence region is an amino acid sequence.

According to still further features in the described preferred embodiments the identifying the anti HIV agent incapable of inducing the mutational instability in the predetermined sequence region of gp120, gp41, and/or CXCR4 is effected in a cell culture being infected with an HIV virus.

According to still further features in the described preferred embodiments the predetermined sequence region of gp120 is selected from the group consisting of C3, C4, V1, V2, V2, V3 and V4.

According to still further features in the described preferred embodiments the predetermined sequence region of gp41 is selected from the group consisting of HR1 and HR2.

According to still a further aspect of the present invention there is provided a method of generating an oligo-saccharide, the method comprising: (a) providing at least two saccharides each having at least one reactive alkyl amino group and protected non-alkyl amino reactive groups; and (b) reacting the at least two saccharides, thereby generating the oligo-saccharide.

According to still further features in the described preferred embodiments reacting the at least two saccharides is effected via a linker.

According to still further features in the described preferred embodiments each of the at least two saccharides is a mono saccharide or an oligosaccharide and whereas at least one saccharide unit in the oligo saccharide.

According to still a further aspect of the present invention there is provided a method of treating a viral infection in a subject, the method comprising providing to a subject in need thereof a pharmaceutical composition including an amino-modified polysaccharide having at least one amino group linked to a peptide composed of at least two basic amino acid residues.

According to still further features in the described preferred embodiments the at least one amino group is an alkyl amino group.

According to still further features in the described preferred embodiments the alkyl amino group is linked to a first saccharide unit of the polysaccharide.

According to still further features in the described preferred embodiments the amino-modified polysaccharide is an aminoglycoside antibiotic.

According to still further features in the described preferred embodiments the aminoglycoside antibiotic is selected from the group consisting of neomycin, kanamycin, sisomycin, fortimycin, paromomycin, neamine and gentamycin.

According to still further features in the described preferred embodiments the basic amino acid residues are selected from the group consisting of arginines, glysines, histidines and combinations thereof.

According to still further features in the described preferred embodiments the peptide is further composed of glutamine and/or aspargine.

The present invention successfully addresses the shortcomings of the presently known configurations by providing novel amino-modified polysaccharides and methods of generating and using thereof in the treatment of viral infections such as AIDS.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The patent or application file contains at least one drawing executed in color. Copies of this patent or patent application publication with color drawing(s) will be provided by the Office upon request and payment of the necessary fee.

In the drawings:

FIG. 1 is a schematic illustration depicting a stepwise process of site-specific arginine conjugation of aminoglycosides.

FIGS. 2a–b are schematic illustrations depicting the structure of aminoglycoside-arginine conjugates and amino-glycosides. All AACs were prepared as acetate salts. FIG. 2a depicts the structures of hexa-arginine neomycin conjugate (NeoR6); a 1:1 mixture of two mono-arginine neomycin conjugates (NeoR1); a di-arginine neomycin conjugate of Neomycin B (NeoR2); a mono-arginine neamine conjugate (NeamR1); a tetra-arginine neamine conjugate (NeamR4); a mono-arginine paromomycin conjugate (ParomR1); and a penta-arginine paromomycin conjugate (ParomR5). FIG. 2b depicts the structure of R3G, a tri-arginine gentamycin C1 conjugate.

FIGs. 3a–c are schematic illustrations depicting the secondary structures of TAR (SEQ ID NO:19, FIG. 3a), RRE IIB (SEQ ID NO:20, FIG. 3b) and the chemical structure of RhdRev fluorescent probe (SEQ ID NO:21, FIG. 3c).

FIGS. 4a–b are graphs depicting the fluorescence anisotropy of fluorescently labeled Rev (RhdRev$_{34-50}$, 10 nM) as a function of TAR RNA concentration (FIG. 4a) or RRE IIB RNA concentration (FIG. 4b).

FIGS. 5a–f are graphs depicting the fluorescence anisotropy of RhdRev 10 nM solution containing TAR RNA (20 nM, FIGS. 5a, 5c and 5e) or RRE IIB RNA (20 nM, FIGS. 5b, 5d and 5f), as a function of the indicated concentrations of NeoR6 (FIGS. 5a–b), ParomR5 (FIGS. 5c–d) or NeamR4 (FIGS. 5e–f).

Figure 6:
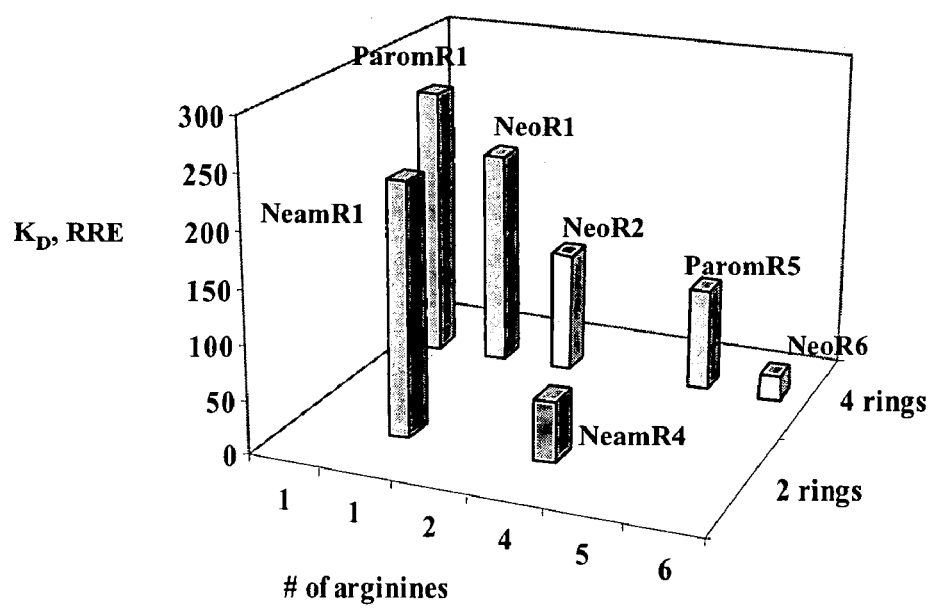

FIG. 6 is a histogram presentation depicting the dependence of the affinity ($K_D$ values) of the AAC/RRE complex on the number of the arginine moieties and rings in the aminoglycoside core.

FIGS. 7a–b are graphs depicting the inhibitory effect of NeoR6 and R3G on the replication of HIV-1 clade C in MT2 cells. MT2 cells were infected for 2 hours at 37° C. in the absence or presence of 2–20 µM NeoR6 (FIG. 7a) or 5–40 µM R3G (FIG. 7b). Infected cells were washed, seeded in 96-well plate (5×10$^4$ cells per well) and incubated for 4 days in the absence or presence of various drug concentrations, until syncytia were observed (>25% ctu). Cell viability was measured by tetrazolium-based colorimetric method. The results shown are mean ±standard deviation of triplicates. Circles denote the presence of AACs during the infection step and after the cells were washed; Squares denote the presence of AACs only during the first 2 hours prior to washing.

FIGS. 8a–b are graphs depicting the inhibitory effect of NeoR6 and R3G on binding of HIV-1$_{IIIB}$ to MT-2 cells (FIG. 8a) and HIV-1 clade C to U937 cells (FIG. 8b). Viral particles of HIV-1$_{IIIB}$ or HIV-1 clade C clinical isolate were radioactively labeled by endogenous reverse transcription (ERT). Following washing of free radioactivity, particles were used to infect the cells. Infection was effected for 2 hours at 37° C. in the presence of the indicated concentrations of NeoR6 (circles) or R3G (squares). Following infection, cells were washed thoroughly and pellet radioactivity was determined.

FIGS. 9a–f are photomicrographs depicting cellular uptake of AACs. Live PM1 cells were incubated for 10 min at room temperature with 0.5 µM of NeoR6-FITC, ParomR5-FITC or NeamR4-FITC. Images were obtained using a Zeiss Axiophot microscope. FIGS. 9a–c are light microscopy images showing the cells in the captured fields. FIGS. 9d–f are the same fields as in FIGS. 9a–c, only a FITC filter was applied.

Figure 10:
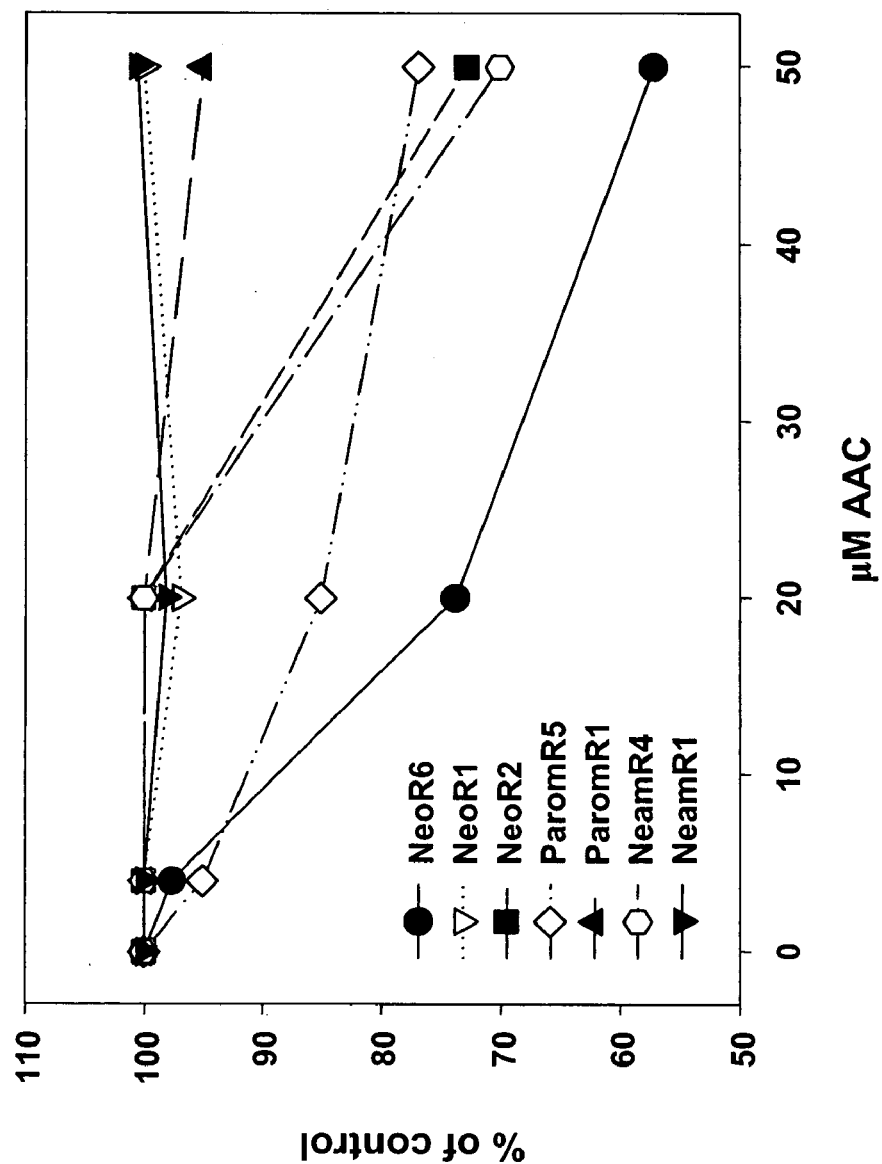
Figure 11:
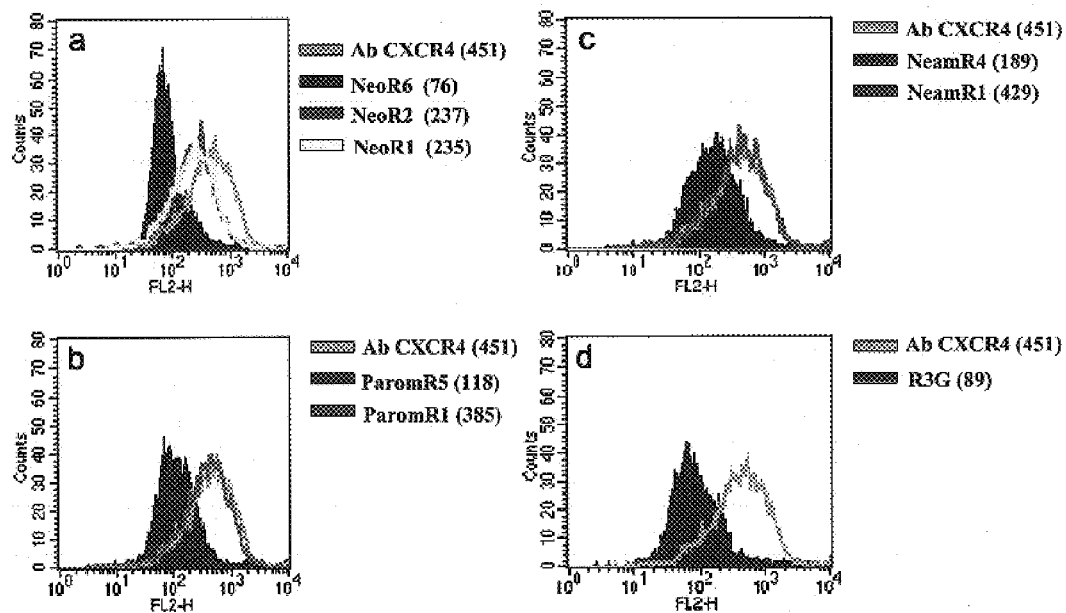
Figure 12:
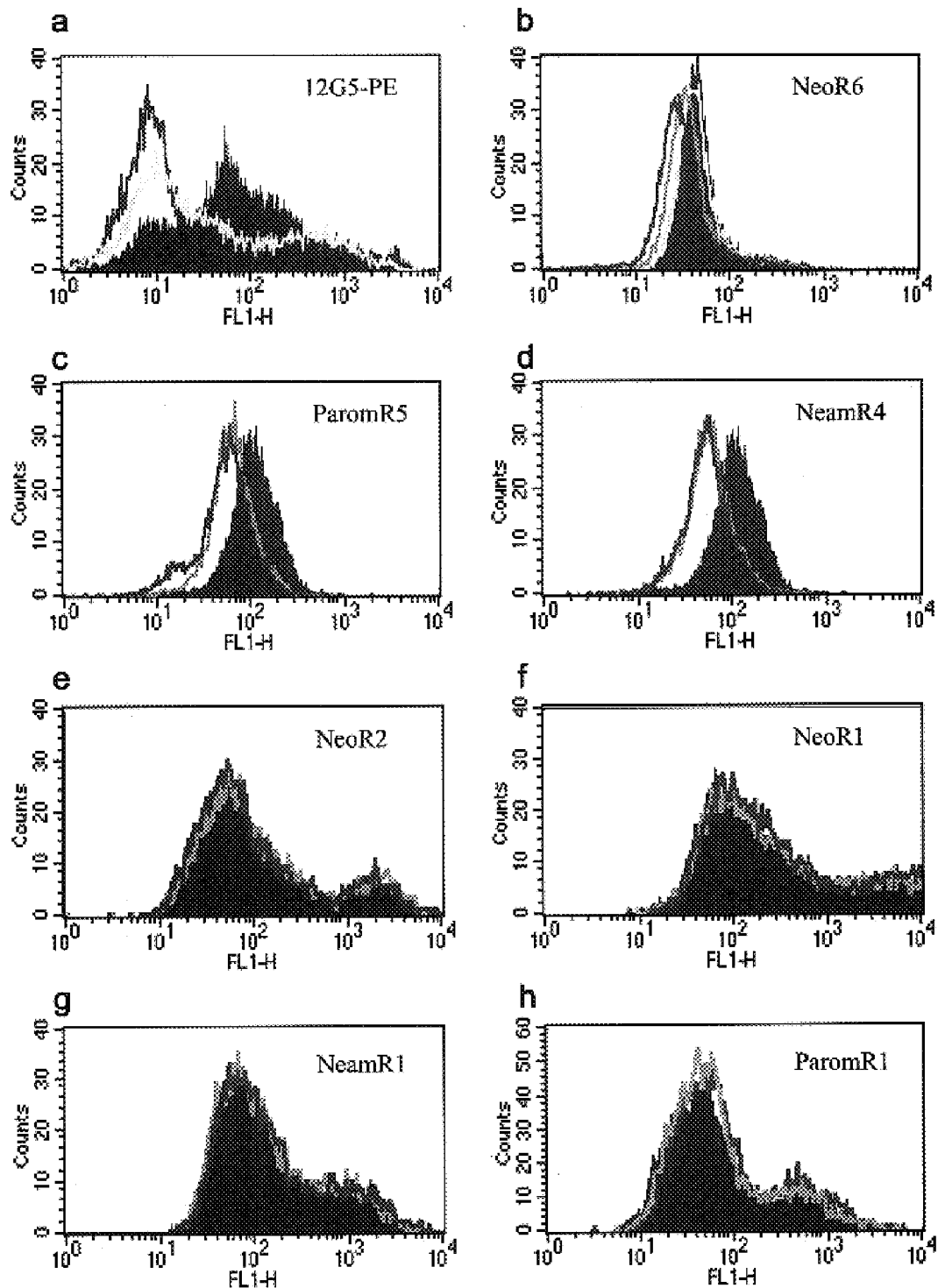

FIG. 10 is a graphic presentation depicting cellular uptake competition of AACs with NeoR6-FITC. NeoR6-FITC (0.5 µM, final concentration) was added to 10$^5$ MT-2 cells (50 µl final volume) alone or in combination with 5, 20 or 50 µM non-labeled AACs. Following 15 minutes of incubation at room temperature, the cells were washed twice with ice-cold PBS and fixed in PBS containing 1% paraformaldehyde. Fluorescence was analyzed using flow cytometry. Note that, the median fluorescence intensity (MFI) of FITC-NeoR6 alone was 62. Similar results were obtained by incubating the cells with the AACs for only 5 minutes.

FIGS. 11a–d are graphs depicting the binding of AACs to CXCR4 in the presence of anti CXCR4 antibody (12G5). PM1 cells were incubated with PE-conjugated isotype control mAb, PE-anti CXCR4 conjugated mAb (12G5) alone, or in the presence of the indicated AACs for 30 min at 4° C. The cells were then washed twice with PBS and analyzed by flow cytometry. The MFI values are shown in parenthesis.

FIGS. 12a–h are graphs depicting inhibition of anti-CXCR4 mAb binding and FITC-labeled AACs entry to PM1 cells by SDF-1α. PM1 cells (10$^5$) were incubated with PE-anti CXCR4 conjugated mAb (12G5, FIG. 12a) or 0.5 µM NeoR6-FITC (FIG. 12b), ParomR5-FITC (FIG. 12c) or NeamR4-FITC (FIG. 12d) in the presence of 0, 62.5, 125 or 250 nM SDF-1α (FIGS. 12a–d, blue, yellow, light blue or red, respectively), or 0.5 µM NeoR2-FITC (FIG. 12e), NeoR1-FITC (FIG. 12f), NeamR1-FITC (FIG. 12g) or ParomR1-FITC (FIG. 12h), in the presence of 0, 250 or 1000 nM SDF-1α (FIGS. 12e–h, red or green, respectively). Following 20 minutes at room temperature the cells were washed twice with PBS and analyzed by flow cytometry.

Figure 13:
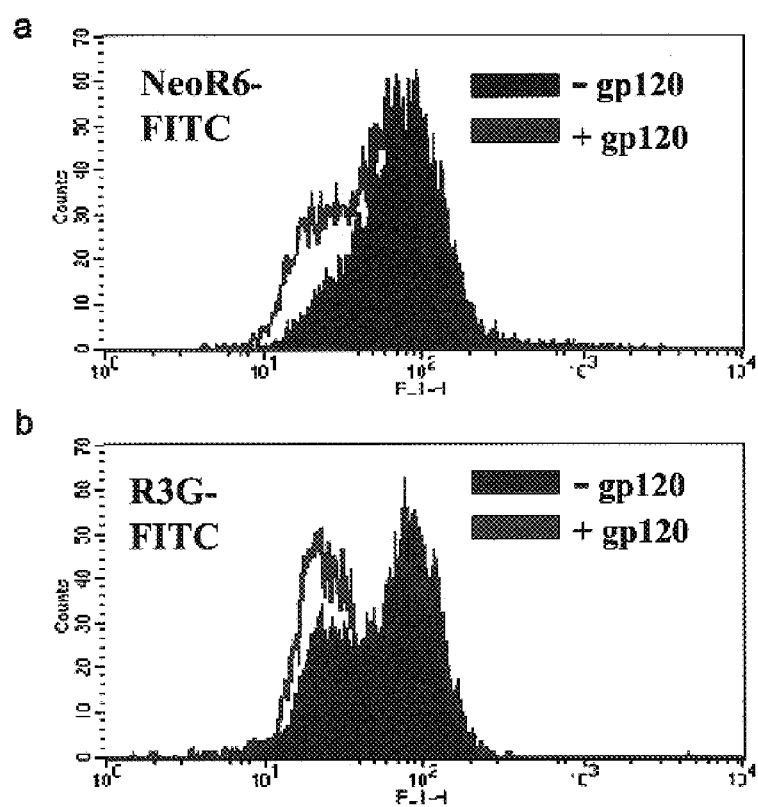

FIGS. 13a–b are graphs depicting the inhibition of NeoR6-FITC (FIG. 13a) and R3G-FITC (FIG. 13b) entry to PM1 cells by HIV-1$_{IIIB}$ gp120. Cells were incubated with 0.5 µM NeoR6-FITC or 0.5 µM R3G-FITC in the absence or presence of 5 µM HIV-1$_{IIIB}$ gp120 for 20 min at room temperature. The cells were then washed twice with PBS and analyzed by flow cytometry.

Figure 14:
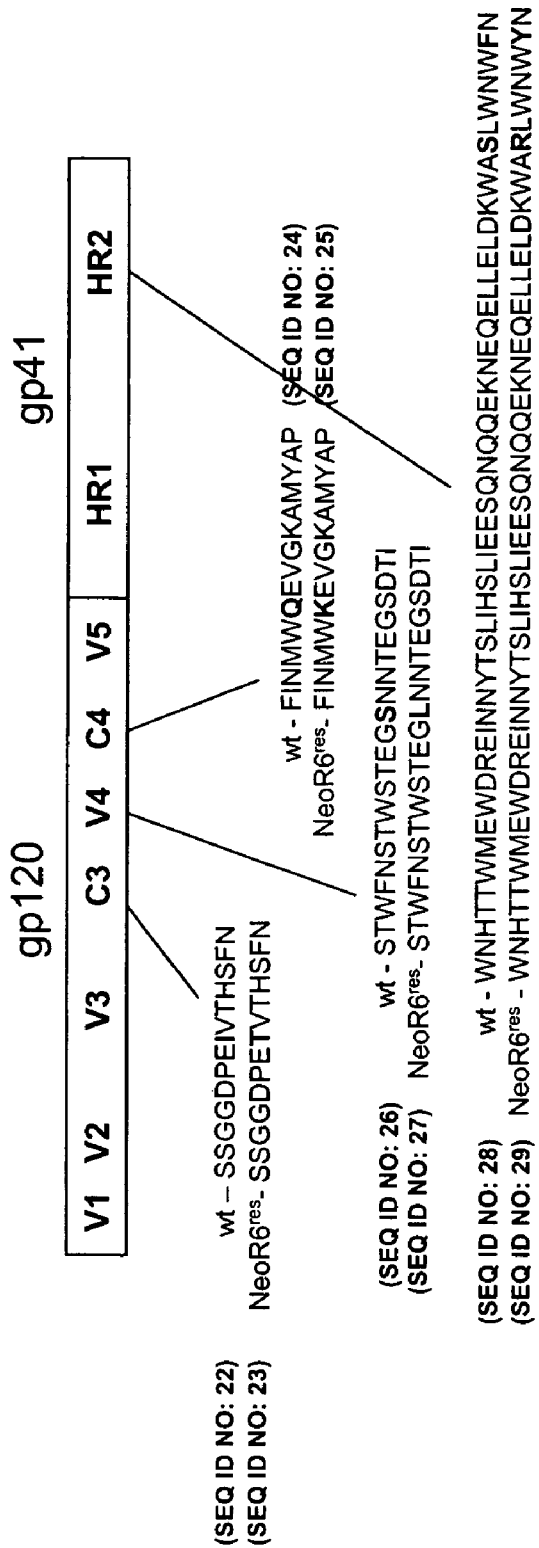

FIG. 14 is a schematic presentation depicting the structure of the gp120 and gp41 HIV-1 proteins having SEQ ID NOS:22–29 (as indicated in the figure) and the positions of the mutations found in NeoR6$^{res}$ isolates.

DESCRIPTION OF THE PREFERRED EMBODIMENTS

The present invention is of amino-modified polysaccharides and methods of generating and using same. Specifically, the present invention employs novel synthesis methodology for generating new amino-modified polysaccharides which can be utilized for the treatment of bacterial and viral infections such as AIDS.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

HIV is the causative agent of acquired immunodeficiency syndrome (AIDS), a fatal human disease, which has affected numerous individuals worldwide. Vast amounts of financial and human resources are currently invested into finding new therapies and new drugs, which may provide some assistance in combating the HIV virus.

Presently, a triple-drug therapy regimen is the most effective approach to controlling the AIDS virus. This "cocktail" includes a combination of a protease inhibitor called indinavir™ with two reverse-transcriptase inhibitors known as AZT™ and 3TC™. The triple drug therapy results in a decrease in measured levels of virus in both blood and lymphatic tissues. However the cocktail therapy is largely restricted by the emergence of resistant viral strains, high costs and long duration of the treatment.

Thus, novel HIV inhibitors directed at HIV targets other than the virus reverse transcriptase and protease are currently sought after.

Various entry inhibitors which direct the gp120 (SPC 3), or gp41 (T20) Env proteins or the CCR5 (RPR 103611, TAK 779) or CXCR4 (T22, T134, ALX40-4C, CGP64222 and AMD 3100) chemokine coreceptors have been recently developed (reviewed in Zaitseva, M. et al., 2003. Biochim. Biophys. Acta 1614: 51–61; De Clercq, E. 2002. Med. Res. Rev. 22: 531–565; De Clercq, E. 1999. Drugs R.D. 2: 321–331; Este, J. A. 2003. Curr. Med. Chem. 10: 1617–1632; Baldwin, C. E. et al., 2003. Curr. Med. Chem. 10: 1633–1642). One of these entry inhibitors, T20 (Trimeris, Durham, N.C.), as been approved for clinical use (M. L. Duffalo and C. W. James, 2003. Enfuvirtide: Novel Agent for the Treatment of HIV-1 Infection. Ann. Pharmacother. 37:1448–1456). However, since these inhibitors target the highly variable viral Env protein, a high strain-to-strain sensitivity variation is expected to occur.

Recently, the trans activating region (TAR) RNA and the Rev responsive element (RRE) both responsible for gene regulation in HIV, have been identified as possible RNA-based drug targets.

The HIV TAR and RRE RNAs were effectively and specifically targeted by aminoglycoside-arginine conjugates (AACs) generated and utilized in a study previously published by the present inventors (WO 00/39139).

Results obtained from that study urged the present inventors to further investigate structural properties which govern AAC binding to RNA, since it was thought that elucidation of these structural properties would enable development of AACs with improved therapeutic efficacy and low cytotoxicity. Specifically, the present inventors set out to identify the role of each of the AAC components (i.e., the aminoglycoside core, the number of arginine moieties and the position of arginine binding to the saccharide) in specific binding to the RNA target. In the course of such an investigation, the present inventors developed a novel approach for selective protection of alkyl amino groups of amino cyclic compounds, which approach can be used for site specific conjugation of chemical moieties to an aminoglycoside core, thus enabling simple and efficient synthesis of novel AACs, which can be used in various therapeutic applications such as in antibacterial and antiviral applications.

Although various approaches for the generation of polyamine analogs, which are selectively modified at the amino functions thereof are known [see, for example, Greene and Wuts (1991) Protective groups in organic synthesis. (II Ed., USA, John Wiley & Sons); Bris (1993) Tetrahedron Lett. 34: 5429–5432], such approaches do not discriminate primary from secondary methylamino functionalities.

Thus, according to one aspect of the present invention there is provided a method of selectively protecting an alkyl amino group of a polyamino cyclic compound.

The method is effected by attaching an N-protecting group to the alkyl amino group of the polyamino cyclic compound. As used herein the phrase "N-protecting group" refers to a chemical group, which is capable of protecting an amino group against undesirable reactions during synthetic procedures.

The N-protecting group of this aspect of the present invention is selected of a spatial size which is suitable for selectively reacting only with the alkyl amino group to thereby selectively protect the alkyl amino group of the polyamino cyclic compound. Thus, the N-protecting group of this method of the present invention is characterized by a relatively large spatial size, as compared with typically used N— protecting groups (e.g., t-Boc).

The size of the N-reacting group is important to the synthesis method of the present invention since, as mentioned hereinabove, protection relies on the difference in proximity of alkyl amines (i.e., alkyl amino groups) and amines (i.e., amino groups) from a backbone; such differential proximity is more significant when a rigid backbone (i.e., cyclic backbone) rather than a linear backbone is used in synthesis.

As used herein the phrase "polyamino cyclic compound" refers to a cyclic compound having a plurality of amino groups including at least one alkyl amino group. Examples of polyamino cyclic compounds include but are not limited to amino saccharides such as natural, synthetic or semi-synthetic aminoglycosides. Examples of aminoglycosides include but are not limited to the aminoglycoside antibiotic, such as, kanamycin, neomycin, seldomycin, tobramycin, kasugamycin, fortimicin, gentamycin, paromomycin, neamine and sisomicin. Examples of semi-synthetic derivatives of aminoglycosides include, but are not limited to, amikacin, netilmicin and the like.

It will be appreciated that cyclic compounds which are devoid of any amino group can also be used according to this aspect of the present invention provided that such cyclic compounds can be chemically modified to include such amino groups. For example, an amino group or groups can be attached to saccharide backbones by methods which are well known in the art, such as by azide displacement on sugar sulphonates or halides.

As mentioned hereinabove, the N-protecting group utilized by the present invention, has a size suitable for selectively reacting with the alkyl amino group and thus, under the synthesis conditions used (see Example 1 of the Examples section) it will not react with other functional groups of the polyamino cyclic compound due to steric effect thereof.

Examples of N-protecting groups, which can be used with the present invention include, but are not limited to, trityl halides such as trityl chloride. Other N-protecting groups which can be used according to thus aspect of the present invention, are disclosed in Greene, "Protective Groups In Organic Synthesis," [John Wiley & Sons, New York (1981)], which is hereby incorporated by reference.

A preferred N-protecting group according to this aspect of the present invention is a trityl group (e.g., trityl chloride), since detritylation cab be effected under very mild reaction conditions, such as in the presence of ytterbium triflate, which does not affect other protected functional groups.

It will be appreciated that when functional groups other than amines (e.g., hydroxyl groups and thiol groups) are present on the cyclic core compound, protection of these groups is preferably effected prior to protection of the alkyl amines described hereinabove, as described in Example 1 of the Examples section. Examples of hydroxyl protecting groups are disclosed by Spivey and Leese [Annu. Rep. Prog. Cham. Sect. B (2002) 98:41–60].

Once selective protection of alkyl amino groups on polyamino cyclic compounds is achieved, such compounds can be used in numerous chemical applications such as for generating a cyclic compound-chemical moiety site specific conjugate.

For example, generation of a saccharide-chemical moiety site-specific conjugate can be effected by providing a saccharide having a reactive alkyl amino group and protected non-alkyl amino reactive groups.

To this end, an amino saccharide which is selectively protected at the alkyl amino groups thereof, such as described hereinabove, is further protected at the amines thereof using typically used amine protecting groups [Spivey and Leese Annu. Rep. Prog. Cham. Sect. B (2002) 98:41–60]. Thus, once all functional groups on the saccharide are protected, a selective deprotection of the alkyl amino group is effected to thereby obtain a saccharide having a reactive alkyl amino group and protected non-alkyl amino reactive groups. Deprotection protocols are well known in the art and the specific procedure is selected according to the protecting group used (see FIG. 1).

Thereafter, the saccharide is reacted with a chemical moiety to thereby generate the saccharide-chemical moiety site specific conjugate.

The chemical moiety can be any moiety which can be reacted with an alkyl amino group either directly or indirectly (via a linker or a cross linker). Typically, acyl halides or alkylhalides are used to react with primary or secondary amines.

Examples of chemical moieties which can be used by the present invention, include but are not limited to, an amino acid (or a polymer thereof) or a saccharide, such as a mono or oligo saccharide.

It will be appreciated that the ability to generate dimeric complexes of AACs is of special significance, since it has been recently suggested that RRE carry two or more aminoglycosite binding sites [Tok (2001) Bioorg. Med. Chem. Lett. 11:1127–31].

The methodology described hereinabove was used by the present inventors to design and synthesize a set of novel aminoglycoside-arginine conjugates.

As is illustrated in the examples section which follows, the present study also included additional conjugates (i.e., ParomR5, NeamR4 and NeoR6), which do not require selective protection of alkyl amino groups and thus were synthesized as previously described for NeoR6 [Litovchick (2001) Biochemistry 40:15612–15623] with some modifications (further described in Example 1 of the Examples section). All these conjugates are listed in Table 1, below.

TABLE 1

| | $R_1$ | $R_2$ | $R_3$ | $R_4$ | $R_5$ | $R_6$ |
|---|---|---|---|---|---|---|
| Neomycin | $NH_2$ | $NH_2$ | $NH_2$ | $NH_2$ | $NH_2$ | $NH_2$ |
| *NeoR6 | Arg | Arg | Arg | Arg | Arg | Arg |
| NeoR1 | Arg | $NH_2$ | $NH_2$ | $NH_2$ | $NH_2$ | $NH_2$ |
| NeoR1 | $NH_2$ | $NH_2$ | $NH_2$ | $NH_2$ | $NH_2$ | Arg |
| NeoR2 | Arg | $NH_2$ | $NH_2$ | $NH_2$ | $NH_2$ | Arg |
| Neamine | $NH_2$ | $NH_2$ | $NH_2$ | $NH_2$ | — | — |
| NeamR1 | Arg | $NH_2$ | $NH_2$ | $NH_2$ | — | — |
| NeamR4 | Arg | Arg | Arg | Arg | — | — |
| Paromomycin | OH | $NH_2$ | $NH_2$ | $NH_2$ | $NH_2$ | $NH_2$ |
| ParomR1 | OH | $NH_2$ | $NH_2$ | $NH_2$ | $NH_2$ | Arg |
| ParomR5 | OH | Arg | Arg | Arg | Arg | Arg |

*Previously described in Litovchick (2001) Biochemistry 40: 15612–15623.
See also FIG. 2.

The novel aminoglycoside arginine conjugates of the present invention in which the core (i.e., neomycin, paromomycin, neamine) and the number of arginine moieties (i.e., 1–6 arginine groups) have been modified, were used by the present inventors to elucidate the mode of antiviral activity of the AACs.

As shown in Table 2 and in Example 3 of the Examples section which follows, dissociation constant analysis and competition assays of AAC binding to TAR and RRE revealed that NeoR6 exhibited the highest affinity to both TAR and $RRE_{IIIB}$ with of $K_D$=5 μM and 23 nM, respectively. ParomR5 and NeamR4 were less active by 3 and 6 folds, respectively in comparison to NeoR6. It will be appreciated that although the mono-arginine derivatives exhibited the lowest affinity to TAR and $RRE_{IIIB}$ ($K_D$=200–500 nM), a conjugation of a single arginine moiety could still exert anti viral activity.

Inhibition of binding of mAb 12G5 or SDF-1α to CXCR4 by each one of the AACs of the present invention, established NeoR6 as the most potent interacting AAC. ParomR5, NeamR4 and NeoR2 or NeoR1 exerted 90%, 70% and 55% of the NeoR6 activity, respectively. The mono-arginine derivatives of paromomycin and neamine inhibited the binding of the mAb to CXCR4 only by 20% and 5.5%, respectively, in comparison to NeoR6.

Thus, the present inventors have found through laborious experimentation a number of parameters which govern high efficacy binding of AACs to HIV targets thereof (i.e., TAR, RRE or CXCR-4, see examples 3–8 of the Examples section, which follows).

These parameters include (i) the number of arginine residues bound to the aminoglycoside core; (ii) the position at which the arginine residue is bound to the aminoglycoside core; and (iii) the nature of the aminoglycoside core.

These findings allow, for the first time, to generate amino modified polysaccharides (e.g., aminoglycoside conjugates), which display improved therapeutic efficacy.

As used herein the phrase "amino modified polysaccharides" refers to molecules which include a polysaccharide core having an amino group which is linked via an amide linkage to an amino acid residue which is preferably basic.

Thus, according to yet another aspect of the present invention there is provided an amino modified polysaccharide, which includes a polysaccharide core modified to include at least one amino group which is linked to at least one peptide including at least two basic amino acid residues.

Such an amino modified polysaccharide differs from prior art aminoglycoside-arginine conjugates (AACs) in that it includes a basic peptide (composed of at least two basic amino acids) linked via a peptide bond to an amino group of a modified polysaccharide; prior art AACs include only a single basic amino acid residue of a single type (arginine).

Since the HIV Tat and Rev molecules are polypeptides, and since the amino acid moiety of aminoglycoside conjugates such as AACs attempts to mimic Tat and Rev binding to viral RNA, inclusion of a basic peptide rather than a single basic amino acid will undoubtably increase the affinity of such aminoglycoside conjugates to the viral target and thus substantially improve efficacy of pharmaceutical composition employing such novel aminoglycoside conjugates.

According to preferred embodiments of this aspect of the present invention the amino group of the aminoglycoside conjugate is an alkyl amino group, which allows a more flexible interaction of the positively charged peptide with the target (e.g., RRE) thereof.

As mentioned hereinabove, the peptide which is linked via the amino group of the polysaccharide, according to this aspect of the present invention, is composed of at least two basic amino acid residues, such as arginines, histidines, lysines, non-natrual derivatives thereof such as D-α-methylarginine, L-α-methylarginine, L-α-methylhistidine, D-α-methylhistidine or a combination thereof.

It will be appreciated that the peptide of the novel aminoglycoside conjugates of the present invention may further include amino acid residues such as glutamine and aspargine which include a free amino group in the side chain.

According to preferred embodiments of this aspect of the present invention the aminoglycoside conjugates is composed of an aminoglycoside antibiotic core which is further described hereinabove.

Preferably the aminoglycoside antibiotic core utilized by the aminoglycoside conjugate of the present invention is neamine, more preferably paromomycin and even more preferably neomycin B.

Preferably the alkyl amino group is linked to the first saccharide unit of the polysaccharide, such as ring I of aminoglycosides (See FIG. 2), since as shown in the Examples section which follows (see Table 2) NeoR6 exhibited a stronger affinity towards the HIV target than ParomR5 suggesting that arginine binding at position 1 of Ring I of the aminoglycoside is highly significant for mediating antiviral activity.

In addition, as is shown in Example 5 of the Examples section which follows, the AAC of the present invention are proven non-toxic to human and mouse cells at a concentration of as much as 500 µM, or when given intravenously in two single doses of 25 mg/kg of body weight over the course of 2 hours (e.g. NeoR6).

As mentioned hereinabove the aminoglycoside conjugate compositions of the present invention can be used in a number of therapeutic applications such as for treating bacterial and viral infections in which the therapeutic efficacy of AACs has been previously implicated (see Background section and Examples 4 and 11 of the Examples section which follows).

Thus, a therapeutically effective amount of the aminoglycoside conjugates of the present invention can be administered to a subject in need thereof to thereby treat the bacterial or viral infections.

The term "treating" refers to alleviating or diminishing a symptom associated with a bacterial or viral infection. Preferably, treating cures, e.g., substantially eliminates, the symptoms associated with the infection and/or substantially decreases the bacterial or viral load in the infected tissue.

Bacterial infections which can be treated using the aminoglycoside conjugates of the present invention include opportunistic aerobic gram-negative bacilli such as the genera *Pseudomonas*, bacterial infection caused by *P. aeruginosa*, bacterial infections caused by gram-positive bacilli such as that of the genus *Mycobacterium*, and mycobacteria, which causes tuberculosis-like diseases. A variety of bacterial infections may be treated by the method of the present invention, these include: *M. tuberculosis, M. leprae, M. Intracellulare, M. smegmatis, M. bovis, M. kansasii, M. avium, M. scrofulcium*, or *M. africanum*.

As is shown in Example 11 of the Example section which follows, Gram-positive bacteria were found to be more susceptible to NeoR6 treatment, displaying MIC values of 0.78–6.25 mg/L.

Thus, according to preferred embodiments of the present invention bacterial infections which are caused by Gram-positive bacteria are preferably treated with the aminoglycoside conjugates of the present invention.

Viral infections which can be treated using the aminoglycoside conjugates of the present invention include but are not limited to HIV infections, infections caused by the equine infectious anemia virus (EIAV) [Litovchick (2000) Biochemistry 39:2838–2852] and hepatitis C viral infections.

It will be appreciated that because of the high exhibited affinity of the aminoglycoside conjugates of the present invention to CXCR-4 (see the Examples section which follows), these compositions may also be used in treating disorders which involve disregulated (e.g., upregulated) function of the chemokine receptor CXCR-4 and/or its cognate ligand stromal cell-derived factor-1 (SDF-1α).

CXCR4 plays an important role in many biological functions, such as B-cell lymphopoiesis, neuronal cell migration and vascular development [Nagasawa et al. (1996) Nature 382, 635–638; Ma et al. (1998) Proc. Natl. Acad. Sci. U. S. A 95, 9448–9453; Zou et al. (1998) Nature 393, 595–599]. SDF-1α, the only known natural ligand of CXCR4, displays important roles in migration, proliferation and differentiation of leukocytes (Bleul et al., 1996; Oberlin et al., 1996).

Disorders which involve abnormal function of CXCR-4 include but are not limited to cancer such as metastatic cancer in which transendothelial cell migration plays a central role in disease progression [Mohle Ann N Y Acad Sci. (1999); 872: 176–85].

The aminoglycoside conjugates of the present invention can be administered to an individual per se, or as part of a pharmaceutical composition where it is mixed with a pharmaceutically acceptable carrier.

As used herein a "pharmaceutical composition" refers to a composition of one or more of the active ingredients described hereinabove, or physiologically acceptable salts or prodrugs thereof, with other chemical components such as physiologically suitable carriers and excipients. The purpose of a pharmaceutical composition is to facilitate administration of a compound to an organism.

Hereinafter, the phrases "pharmaceutically acceptable carrier" and "physiologically acceptable carrier" are used interchangeably to refer to a carrier or a diluent that does not cause significant irritation to a treated individual and does not abrogate the biological activity and properties of the active ingredient.

Herein the term "excipient" refers to an inert substance added to a pharmaceutical composition to further facilitate administration of active ingredients. Examples, without limitation, of excipients include calcium carbonate, calcium phosphate, various sugars and types of starch, cellulose derivatives, gelatin, vegetable oils and polyethylene glycols.

Techniques for formulation and administration of the pharmaceutical compositions of the present invention may be found in "Remington's Pharmaceutical Sciences," Mack Publishing Co., Easton, Pa., latest edition, which is incorporated herein by reference.

Suitable routes of administration may, for example, include oral, rectal, transmucosal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a pharmaceutical composition in a local rather than systemic manner, for example, via injection of the composition directly into the area of infection often in a depot or slow release formulation, such as described below.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredient into compositions which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the pharmaceutical composition can be formulated by combining the active agents with pharmaceutically acceptable carriers well known in the art. Such carriers enable the pharmaceutical composition used by the method of the invention to be formulated as tablets, pills, dragees, capsules, liquids, gels, syrups, slurries, suspensions, and the like, for oral ingestion by a patient. Pharmacological compositions for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose compositions such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the agents for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient and a suitable powder base such as lactose or starch.

Ophthalmic formulations, eye ointments, powders, solutions and the like, are also contemplated as being within the scope of this invention.

The compositions described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active ingredient in water-soluble form. Additionally, suspensions of the active ingredient may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or formulations, which increase the solubility of the active ingredient to allow for the composition of highly concentrated solutions.

Alternatively, the active ingredient may be in powder form for constitution with a suitable vehicle, e.g., sterile, pyrogen-free water, before use.

The composition of the present invention may also be formulated in rectal compositions such as suppositories or retention enemas, using, e.g., conventional suppository bases such as cocoa butter or other glycerides.

In addition to the formulations described previously, a composition of the present invention may also be formulated for local administration, such as a depot composition. Such long acting formulations may be administered by implantation (for example subcutaneously or intramuscularly) or by intramuscular injection. Thus, for example, the composition may be formulated with suitable polymeric or hydrophobic materials (for example, as an emulsion in an acceptable oil) or ion exchange resins, or as sparingly soluble derivatives such as sparingly soluble salts. Formulations for topical administration may include, but are not limited to, lotions, suspensions, ointments gels, creams, drops, liquids, sprays emulsions and powders.

The pharmaceutical compositions herein described may also comprise suitable solid of gel phase carriers or excipients Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of active ingredient effective to prevent, alleviate or ameliorate symptoms of disease or prolong the survival of the subject being treated.

Determination of a therapeutically effective amount is well within the capability of those skilled in the art.

For any composition used by the methods of the invention, the therapeutically effective amount or dose can be estimated initially from cell culture assays and cell-free assays (See Example 5 of the Example section which follows). For example, a dose can be formulated in animal models to achieve a circulating concentration range that includes the $IC_{50}$ as determined in in-vitro assays and/or to determine the maximum tolerated dose (MTD) in animal models as described in Example 5 of the Examples section which follows. Such information can be used to more accurately determine useful doses in humans.

Therapeutic doses can be provided as a one-time administration or as multiple-administrations with or without an intervening period of no treatment.

Regardless, toxicity and therapeutic efficacy of the pharmaceutical compositions described herein can be determined by standard pharmaceutical procedures in experimental animals, e.g., by determining the $IC_{50}$ and the $LD_{50}$ (lethal dose causing death in 50% of the tested animals) for a subject ingredient. The data obtained from assays can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active ingredient, which are sufficient to maintain the required effects, termed the minimal effective concentration (MEC). The MEC will vary for each composition, but can be estimated from in vitro data; e.g., the concentration necessary to achieve 50–90% inhibition, (see Example 1 of the Examples section). Dosages necessary to achieve the MEC will depend on individual characteristics and route of administration. HPLC assays or bioassays can be used to determine plasma concentrations.

Dosage intervals can also be determined using the MEC value. Compositions should be administered using a regimen, which maintains plasma levels above the MEC for 10–90% of the time, preferable between 30–90% and most preferably 50–90%.

It is noted that, in the case of local administration or selective uptake, the effective local concentration of the drug may not be related to plasma concentration. In such cases, other procedures known in the art can be employed to determine the effective local concentration.

Depending on the severity and responsiveness of the infection to be treated, dosing can also be a single administration of a slow release composition, with course of treatment lasting from several days to several weeks or until cure is effected or diminution of the infection state is achieved.

The amount of a composition to be administered will, of course, be dependent on the subject being treated, the severity of the infection, the manner of administration, the judgment of the prescribing physician, etc.

Compositions of the present invention can be packaged in a dispenser device, as one or more unit dosage forms as part of an FDA approved kit, which preferably includes instruction for use, dosages and counter indications. The kit can include, for example, metal or plastic foil, such as a blister pack suitable for containing pills or tablets, or a dispenser device suitable for use as an inhaler. The kit may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising an active ingredient suitable for use with the present invention may also be prepared, placed in an appropriate container, and labeled for treatment of an indicated disease or condition.

Drug resistance is a growing problem encountered with all classes of antibiotics and antiviral drugs Drug-resistant human immunodeficiency virus (HIV)-1 has been detected in patients on all of the currently available antiretroviral drug regimens. Continuous, high-level virus replication with an error-prone reverse transcriptase enzyme and potential viral recombination events lead to each patient having numerous viral quasispecies and promote the emergence of drug-resistant strains. Drug resistance is associated with one or more point mutations in the HIV gene of the protein that is targeted by the drug. Factors associated with rapid emergence of drug resistance include host factors, such as advanced HIV disease and low CD4 cell counts; viral factors, such as high plasma HIV RNA, pre-existing drug-resistant virus, and possibly syncytium-inducing (SI) phenotype; and drug-related factors, such as suboptimal drug levels or poor compliance. High-level drug resistance has emerged after weeks to months of therapy for lamivudine (3TC) and nevirapine where drug-resistant quasispecies pre-exist in essentially all patients. Resistance has emerged more slowly for zidovudine (ZDV) and HIV protease inhibitors, which require the sequential accumulation of multiple mutations to develop high-level resistance. Certain drugs, such as didanosine (DDI), dideoxycytidine (DDC), and stavudine (D4T) have only produced viruses with low-level resistance, despite prolonged therapy. Development of drug-resistant HIV-1 has been associated with declining CD4 cell counts and rising plasma viral load. Zidovudine-resistant HIV-1 has been associated with adverse clinical outcomes independent of baseline CD4 cell counts and plasma HIV-1 RNA levels [Meyers (1997) Am. J. Med. 102(5B): 70–5].

Thus, identification of putative anti HIV agents is a preliminary but yet insufficient step towards efficient antiviral combating, due to the ability of the virus to overcome the inhibitory effects of the antiviral agent by mutating target genes.

As is shown in Example 9 of the Examples section which follows, the present inventors have identified through laborious experimentation HIV-1 isolates which are resistant to high concentrations of NeoR6 for at least 25 passages. Moreover, as is shown in FIG. 14, Table 6 and Example 10 of the Examples section which follows, the present inventors have uncovered mutations in the C3, V4 and C4 regions of the gp120 protein and in the HR2 region of the gp41 protein of the HIV-1 virus which enabled the resistance of the HIV-1 virus to the high concentrations of NeoR6. The identification of such mutations strongly suggest that NeoR6 obstructs HIV-1 infection by interfering with the fusion step, dependent of both conformational changes in gp120 following CD4 and CXCR4 interaction, as well as by conformational changes in gp41 induced by HR1 and HR2 interaction. These results demonstrate the generation of HIV inhibitor-resistant clones and the use of sequencing of the gp120 and/or gp41 genes in such clones in order to reveal the inhibitor-escape mechanism.

Thus, according to an additional aspect of the present invention, there is provided method of identifying a potent anti HIV agent.

As used herein the phrase "potent anti HIV agent" refers to a drug which exhibits durable long lasting anti HIV activity.

The method is effected by first providing a plurality of putative anti HIV agents. Thereafter, agents which are incapable of inducing mutational instability in a predetermined sequence region of gp120, gp41 and/or CXCR4 are identified, thereby identifying the potent anti HIV agent.

It is highly likely that agents which do not promote a viral escape pathway i.e., "mutational instability" will attenuate and optimally even prevent the emergence of resistant strains.

The putative anti HIV agents according to this aspect of the present invention are biological or chemical agents obtained by combinatorial screening of chemical, antibody or peptide libraries, using methods which are well known in the art.

Typically, the putative anti HIV agents used according to this aspect of the present invention are entry inhibitors, [Michael, N. L. & Moore, J. P. (1999) Nat. Med. 5, 740–742; and Moore, J. P. & Stevenson, M. (2000) Nat. Rev. Mol. Cell Biol. 1, 40–49] such as the gp120-targeted recombinant protein CD4-IgG2, the SPC 3 and T20 synthetic peptides, the RPR 103611, TAK 779, T22, T134, ALX40-4C, CGP64222 and AMD 3100 low molecular weight non-peptide antagonists (reviewed in Zaitseva, M. et al., 2003. Biochim. Biophys. Acta 1614: 51–61; De Clercq, E. 2002.

Med. Res. Rev. 22: 531–565; De Clercq, E. 1999. Drugs R. D. 2: 321–331; Este, J. A. 2003. Curr. Med. Chem. 10: 1617–1632; Baldwin, C. E. et al., 2003. Curr. Med. Chem. 10: 1633–1642), the chemokine derivative AOP-RANTES, small molecules (e.g., bicyclam, AACs), peptides, and mAbs specific for the chemokine receptors CXCR4 and CCR5 [reviewed in Michael, N. L. & Moore, J. P. (1999) Nat. Med. 5, 740–742; and Moore, J. P. & Stevenson, M. (2000) Nat. Rev. Mol. Cell Biol. 1, 40–49].

The putative anti HIV agents of the present invention can be also designed or further optimized using rational drug design.

Rational drug design is a potent means of identifying enzyme inhibitors. Such an approach has been used to identify HIV protease inhibitors (Lam et al., 1994. Science 263, 380; Wlodawer et al., 1993. Ann Rev Biochem. 62, 543; Appelt, 1993. Perspectives in Drug Discovery and Design 1, 23; Erickson, 1993. Perspectives in Drug Discovery and Design 1, 109), and bcr-abl tyrosine kinase inhibitors (Mauro M J. et al., 2002. J Clin Oncol. 20, 325–34), the first effective pharmacological cures for human acquired immunodeficiency syndrome (AIDS) caused by human immunodeficiency virus (HIV) and a human cancer (chronic myeloid leukemia), respectively.

Examples of suitable chemical structure databases for identifying or optimizing the putative anti HIV agents of the present invention include ISIS (MDL Information Systems, San Leandro, http://www.molinfo.com), MACCS-3D (Martin, Y. C., 1992. J. Med. Chem. 35, 2145–2154), The Cambridge Structural Database (CSD; http://www.ccdc.cam.ac.uk/prods/csd/csd.html), Fine Chemical Database (reviewed in Rusinko A., 1993. Chem Des Auto. News 8, 44–47), and the NCBI's Molecular Modeling DataBase: MMDB; http://www.ncbi.nlm.nih.gov/Structure/MMDB/mmdb. shtml.

To identify the putative anti HIV agents via de novo rational drug design, or via modification of a known chemical structure, software comprising "builder" type algorithms utilizes a set of atomic coordinates defining a three-dimensional structure of the binding pocket and the three-dimensional structures of basic chemical building blocks to computationally assemble a putative inhibitor. Such an approach may be employed to structurally refine the putative anti HIV agents identified using the guidelines described hereinabove, for example, via chemical database screening as described above.

Ample guidance for performing rational drug design via software employing such "scanner" and "builder" type algorithms is available in the literature of the art (for example, refer to: Halperin I. et al., 2002. Proteins 47, 409–43; Gohlke H. and Klebe G., 2001. Curr Opin Struct Biol. 11, 231–5; Zeng J., 2000. Comb Chem High Throughput Screen. 3, 355–62; and RACHEL: Theory of drug design, http://www.newdrugdesign.com/Rachel_Theory.htm#Software), and described in further detail hereinbelow.

Criteria employed by software programs used in rational drug design to qualify the binding of screened chemical structures with binding pockets include gap space, hydrogen bonding, electrostatic interactions, van der Waals forces, hydrophilicity/hydrophobicity, etc.

Contact area between compounds may be directly calculated from the coordinates of the compounds in docked conformation using the MS program (Connolly M L., 1983. Science 221, 709–713).

Suitable software employing "scanner" type algorithms include, for example, docking software such as GRAM, DOCK, or AUTODOCK (reviewed in Dunbrack et al., 1997. Folding and Design 2, 27), AFFINITY software of the INSIGHTII package (Molecular Simulations Inc., 1996, San Diego, Calif.), GRID (Goodford P J., 1985. "A Computational Procedure for Determining Energetically Favorable Binding Sites on Biologically Important Macromolecules", J. Med. Chem. 28, 849–857; GRID is available from Oxford University, Oxford, UK), and MCSS (Miranker A. and Karplus M., 1991. "Functionality Maps of Binding Sites: A Multiple Copy Simultaneous Search Method", Proteins: Structure Function and Genetics 11, 29–34; MCSS is available from Molecular Simulations, Burlington, Mass.).

Programs employing "builder" type algorithms include LEGEND (Nishibata Y. and Itai A., 1991. Tetrahedron 47, 8985; available from Molecular Simulations, Burlington, Mass.), LEAPFROG (Tripos Associates, St. Louis, Mo.), CAVEAT (Bartlett, P A. et al., 1989. Special Pub Royal Chem Soc. 78, 182–196; available from University of California, Berkeley), HOOK (Molecular Simulations, Burlington, Mass.), and LUDI (Bohm H J., 1992. J. Comp Aid Molec Design 6, 61–78; available from Biosym Technologies, San Diego, Calif.).

During or following rational drug design, docking of an intermediate chemical structure or of the putative inhibitor with the binding pocket may be visualized via structural models, such as three-dimensional models, thereof displayed on a computer screen, so as to advantageously allow user intervention during the rational drug design to optimize a chemical structure.

Software programs useful for displaying such three-dimensional structural models, include RIBBONS (Carson, M., 1997. Methods in Enzymology 277, 25), O (Jones, T A. et al., 1991. Acta Crystallogr. A47, 110), DINO (DINO: Visualizing Structural Biology (2001) http://www.dino3d.org); QUANTA, INSIGHT, SYBYL, MACROMODE, ICM, MOLMOL, RASMOL and GRASP (reviewed in Kraulis, J., 1991. Appl Crystallogr. 24, 946), TAR-NeoR6 complex model (Litovchik et al., 2001, Biochemistry, 40: 15612–15623) and the TAR-AAC complex model by enzymes and chemical degradation [Litovchik et al., (2000) Supra].

Other molecular modeling techniques may also be employed in accordance with this invention (for example, refer to: Cohen N C. et al, 1990. "Molecular Modeling Software and Methods for Medicinal Chemistry", J. Med. Chem. 33: 883–894; Navia M. A. and Murcko M. A., 1992. "The Use of Structural Information in Drug Design", Current Opinions in Structural Biology 2: 202–210). For example, where the structures of test compounds are known, a model of the test compound may be superimposed over the model of the structure of the invention. Numerous methods and techniques are known in the art for performing this step, any of which may be used (for example, refer to: Farmer P. S., "Drug Design", Ariens E J. (ed.), Vol. 10, pp 119–143 (Academic Press, New York, 1980); U.S. Pat. No. 5,331, 573; U.S. Pat. No. 5,500,807; Verlinde C., 1994. Structure 2, 577–587; and Kuntz I D., 1992. Science 257, 1078–108).

For example, a cell line tropic HIV strain such as the HIV-1 NL4.3 (obtainable from the National Institute of Allergy and Infectious Disease AIDS reagent program) can be passaged in cells which express the chemokine receptor CXCR-4 (e.g., MT-4 cells; Schols Supra) or which were modified to express the entry receptor in the presence of the putative anti HIV agents at a starting concentration such as corresponding to 50% inhibitory concentration ($IC_{50}$).

Every 4–5 days, mutational instability in a predetermined sequence of the CXCR-4 host entry receptor, gp120, or gp41 viral gene can be detected in the presence of gradually growing concentrations of the antiviral agents.

Mutational instability at predetermined sequence regions can be detected at the nucleic acid sequence levels (i.e., DNA, RNA) or amino acid sequence level using methods which are well known in the art such as DNA sequencing, amplification techniques (e.g., PCR), hybridization techniques (e.g., Northern blotting, Southern blotting, Western blotting), trypsin cleavage and the like [see "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988)]. Analysis is preferably effected along side a wild type gp120, gp41 or CXCR-4 sequence analysis which is used for control.

Mutational instability in gp120 can be detected in the V1–V3 loop regions as was previously described for HIV entry inhibitors (de Vreese (1996) Supra; and Schols (1998) Supra). Alternatively or additionally, as is demonstrated in Example 11 of the Examples section which follows, mutational instability is detected at the constant regions C3 and C4 and in the variable region V4 of gp120, which may affect viral entry through the CXCR-4 or through alternative pathways such as through CCR5 [Mondor (1998) Virology 248:394–405; Trkola (1996) Nature 384:184–187; Wu (1996) Nature 384:179–183].

Mutational instability in gp41 can be detected in the HR1 and HR2 regions as is shown in Example 11 of the Example section which follows.

Mutational instability in CXCR-4 is preferably detected at the SDF-1α binding site (GenBank Accession No.: P30991), since as shown in Examples 7–9 of the Examples section which follows, AACs of the present invention compete with SDF-1α binding to the CXCR-4 receptor, indicating a common binding site.

Once anti HIV agents which do not exert mutational instabilities (e.g., after 4–5 days) are identified they are considered as potent anti HIV agents according to this aspect of the present invention.

It will be appreciated that these potent anti HIV agents are preferably used in combination therapy with other anti HIV agents, since it is well known that combination therapy offers means of delaying or preventing the development of HIV drug resistance.

In conclusion, AACs are multifunctional anti-viral inhibitors. They exert their antiviral activity not only via obstruction of key HIV-1 transcriptional events, but also by hampering early steps in the viral cycle of T-tropic HIV-1, through interference of the interaction of gp120 with CXCR4. Among the AAC of the present invention, the NeoR6 is the most active AAC. These results indicate that the number of arginines attached, as well as the core itself are important for their capacity in interfering with gp120-CXCR4 interaction.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Site Specific Conjugation Of Arginine Residuese to Aminoglycosides

Attempts to prepare mono- and di-arginine conjugates of aminoglycosides without protection of the amino and hydroxyl groups revealed variable mixtures of arginine conjugates and unreacted aminoglycoside. Thus, a novel strategy for site-specific arginine conjugation to aminoglycosides was undertaken.

Despite widespread use, current methods for selective protection of amines in the presence of polyamine analogs are laborious [Bradshaw (1992) Tetrahedron 48, 4475–4515]. Furthermore, although many synthetic protocols have been described for selective protection of the amino functions of polyamines with groups such as methylene, p-toluenesulphonyl (tosyl), tert-butoxycarbonyl (Boc), benzyloxycarbonyl (Cbz), phthalyl (Phth) [Greene (1991). Protective Groups in Organic Synthesis. (II Ed., USA: John Wiley & Sons)] and metal cations [Bris (1993) Tetrahedron Lett. 34, 5429–5432] all these protocols do not discriminate primary from secondary methylamino functions.

The key feature of the present approach towards selective acylation of the primary methylamino groups is the spatial proximity difference between primary and secondary methylamino moieties. Various attempts have been taken for direct tritylation of aminoglycosides, however this approach turned out to be not suitable due to rapid hydrolysis of trityl chloride in aqueous medium. Similarly, the use of direct benzylation of hydroxyl group in aqueous medium is also unfeasible. Since aminoglycosides solubility in most organic solvents is very poor, modification of these molecules to increase their solubility in organic solvents was essential.

Figure 1:
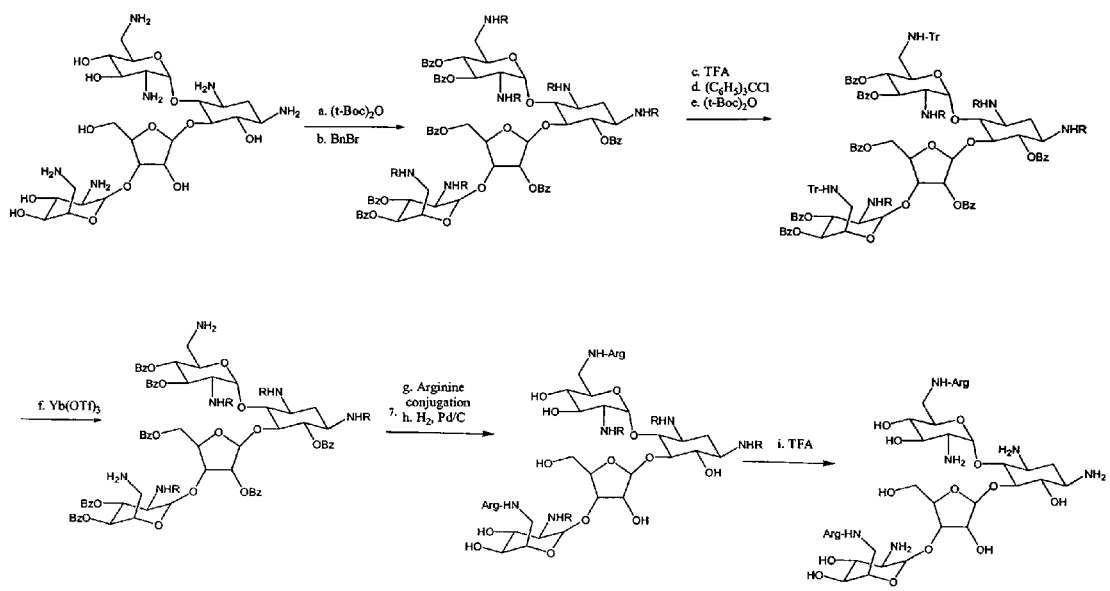

The procedure presented in FIG. 1 illustrates the various steps of the synthesis. Protection of all the aminoglycoside amines by Boc-anhydride [FIG. 1, step (a)] is followed by protection of hydroxyl groups by benzyl bromide in anhydrous DMF [FIG. 1, step (b)]. Removal of the Boc groups by trifluoroacetic acid [TFA, FIG. 1, step (c)], whereas the primary methylamines are protected by trityl chloride [FIG. 1, step (d), Krakowiak (1998) Synthetic Commun. 28: 34513459] and all the secondary methylamines are protected again by using Boc-anhydride [FIG. 1, step (e)]. The selectivity of N-tritylation is achieved due to the bulkiness of the trityl group, which attacks the primary methylamines rather than secondary ones, while Boc-anhydride does not discriminate between primary and secondary methylamines. Trityl group selection for protection is effected according to the spatial proximity difference between primary and secondary methylamines and the conditions for the detritylation process [FIG. 1, step (f)] which is effected in very mild conditions using ytterbium triflate [Lu (2000) Tetrahedron Lett. 41, 2817–2819.], which does not affect other protected amines and hydroxyls.

Materials and Experimental Procedures

Neomycin B and paromomycin were purchased from Sigma as sulphate salt and were used as free base aminoglycosides. 1[3-Dimethylaminopropyl]-3-ethylcarbodiimide hydrochloride was obtained from Aldrich. $N(\alpha)$-carbobenzoxy-$N(\omega)$-nitro-L-arginine and barium chloride were purchased from Fluka and N,N'-dicyclohexylcarbodiimide (DCC) from Merck. Activated palladium on charcoal (Pd/C; 10%) was obtained from BDH. All other reagents were used without further purification, except dimethylformamide that was distilled and dried over molecular shieves before use. Neamine was prepared as previously reported [Park (1996) J. Am. Chem. Soc. 118, 10150–10155]. The obtained neamine hydrochloride was converted to a free base by running the aqueous solution of neamine hydrochloride through anion exchanger resin AG-MP 1 (OH form) column and the collected fraction was dried under vacuo, precipitated with alcohol and dried.

$^1$H NMR spectrum analysis—Intermediate and final products were analyzed by the Bruker AMX-400 (400 MHz) NMR Spectrophotometer at ambient temperature.

Mass spectrum analysis—Mass spectra were recorded using Micromass Platform LCZ 4000-Electro Spray Ionization mode and MALDI-TOF MS.

Synthesis of Site-Specific Arginine-Aminoglycoside Conjugations ($R_1$ and $R_6$) of Neomicin, Paromomycin and Neamine: General Procedure I (FIG. 1).

1. Amine Protection: FIG. 1, Step (a)

Approximately 5 mmol of water: dioxan:alcohol (1:1:1) solution of free base aminoglycoside was used for the preparation of the aminoglycoside-arginine conjugates. One equivalent of each amino group of the aminoglycoside was treated with 1.5 equivalents of di-tert-butyldicarbonate (Boc-anhydride) in dioxane:water (1:1 v/v), sodium hydroxide (1M) solution was added slowly to keep the reaction mixture at pH>10 and stirring was continued for 24 hours. The solvents were removed in vacuo and Boc-derived aminoglycoside was dissolved in ethyl acetate. The organic layer was extracted with water and brine repeatedly until all the sodium hydroxide was washed off. The ethyl acetate solution was dried over $Na_2SO_4$, the white residue was purified by silica gel column chromatography using n-hexane:ethyl acetate (4:1 v/v) as an eluent. The obtained product (yield ~85%) was tested with ninhydrin to verify that no free amino groups left. $^1$H NMR spectrum was measured in $CDCl_3$ and the methyl protons of Boc was observed at 1.29 ppm as a broad singlet. Mass spectroscopy ESI m/z for hexa-Boc-neomycin found 1215.96, calculated 1215; (M+Na$^+$) 1238.11, calculated 1238; for penta-Boc-paromomycin found 1116.623 (M+1) 1117.76, calculated for M 1116; for tetra-Boc-neamin found 723.36 calculated 723, (M+N$_a^+$) 745.7 calculated 745.

2. Hydroxyl Protection: FIG. 1, Step (b)

One equivalent of each hydroxyl group of aminoglycoside was treated with 2 equivalents of benzyl bromide, 0.5 equivalent of tert-butyl ammonium iodide and 1.5 equivalents of sodium hydride in anhydrous DMF. Sodium hydride was added slowly for 3 hours and the reaction was allowed to continue for another 24–48 hours. The progress of the reaction was monitored by silica gel plated thin layer chromatography (TLC) using n-hexane:ethyl acetate (4:1 v/v) as a running buffer. After completion of the reaction, DMF was removed under high vacuo and the O-benzylated aminoglycoside was extracted with ethyl acetate, the organic layer was washed with water and brine, dried over $Na_2SO_4$ and purified by silica gel column chromatography and n-hexane:ethyl acetate (5:1 v/v) as an eluent. The obtained product (yield~73%) was analyzed by $^1$H NMR spectra in $CDCl_3$, the signal of phenol ring of benzyl moiety was observed at 7.3 ppm as a multiplet and the methylene signal of benzyl group was observed at 3.7 ppm as a singlet.

3. Deprotection of Boc: FIG. 1, Step (c)

Deprotection of Boc was achieved by trifluoroacetic acid. N-boc-O-benzyl aminoglycoside was dissolved in dichloromethane:trifluoroacetic acid (10:1 v/v) mixture and stirring was continued until all the Boc groups were removed, as confirmed by $^1$H NMR spectroscopy. After completion of deprotection of the amine functional groups, the solvents were removed in vacuo. Traces of trifluoroacetic acid (TFA) were evaporated with carbon tetrachloride prior to product purification. The ethyl acetate solution of the compound was washed with water and dried over $Na_2SO_4$. The ethyl acetate phase was stirred with charcoal at 45° C. for 15 minutes and then purified by silica gel filtration column, the eluent was evaporated, affording pure product (yield~69%). The $^1$H NMR spectrum of the product (in $CDCl_3$) confirmed the absence of Boc peak at 1.29 ppm, and ninhydrin test supported this result.

4. N-Tritylation: FIG. 1, Steps (d, e)

To a solution of O-benzylated aminoglycoside (1 equivalent per amino group) and triethylamine (2 eq.) in chloroform, trityl chloride (1.5 eq.) in chloroform was added slowly with stirring at room temperature, stirring was continued for 12 hours. The reaction mixture was washed with water and dried over $Na_2SO_4$. The chloroform was evaporated and the residue was purified by silica gel column chromatography using n-hexane:ethyl acetate:methanol (4:1:0.5 v/v) mixture as an eluent. The $^1$H NMR (in $CDCl_3$) spectra of the final product confirmed the presence of trityl signal at 7.1–7.5 as a multiplet. Yield: ~43%. The secondary methylamines are blocked again by Boc anhydride.

5. N-Detritylation: FIG. 1, Step (f)

N-tritylated aminoglycoside was treated with a catalytic amount (0.2 mol equivalent) of ytterbium triflate [$Yb(OTf)_3$] in tetrahydrofuran containing 1 equivalent of water at room temperature. The $^1$H NMR spectra (in $CDCl_3$) confirmed the absence of trityl signal at 7.1–7.5 ppm Yield: ~80%

6. Arginine Conjugation: FIG. 1, Step (g)

The obtained product after removal of trityl group was dissolved in dioxane:chloroform (1: 1 v/v) and was reacted with N($\alpha$)-carbobenzoxy-N($\omega$)-nitro-L-arginine (1.5 eq. for each primary methylamino group of the aminoglycosides at position $R_1$ or $R_6$) and dicyclohexylcarbodiimide (2 eq.) added in 4 portions during three hours, stirring was continued for 48 hours at room temperature. The course of the reaction was followed by ninhydrin test as well as by silica plated TLC using n-hexane:ethyl acetate:methanol (2:1:0.5 v/v) as an eluent. After completion of the reaction, the precipitate was filtered off and the solvents were evaporated in vacuo. The obtained precipitate of the aminoglycoside-arginine conjugate was repeatedly washed with 0.1 M sodium hydroxide solution and water.

7. Hydrogenation: FIG. 1, Steps (h, i)

The protected arginine-aminoglycoside conjugate was dissolved in dioxane:methanol (1:1 v/v), and was hydrogenated at atmospheric pressure with 10% Pd/C for 6 hours to remove carbobenzoxy- and nitro- groups. The catalyst Pd/C was then filtered off, fresh Pd/C was added and the hydrogenation was continued for another 3 hours. After completion of the hydrogenation, the catalyst was filtered off, solvents were evaporated in vacuo. The obtained compound was treated with TFA in the presence of acetic acid (2 eq. per free amino group) for 30 minutes and the excess of acetic acid was removed under vacuo. Finally, the arginine conjugate aminoglycoside was precipitated by absolute alcohol as a white powder acetate salt.

Synthesis of Per-Arginine-Aminoglycoside Conjugates of Paromomycin, Neamin and Neomycin B: General Procedure II Free base aminoglycosides were prepared by removing the sulphate anion by barium chloride from the commercially available aminoglycoside sulphate. The clear aqueous layer was passed through anion exchanger AG-MP 1 (OH form) column. Approximately 5 mmol of free base aminoglycoside solution (alcohol:dioxane:water 1:1:1 v/v) was used for the preparation of the aminoglycoside arginine conjugates. For each amino group of the aminoglycoside, a mixture of 1.5 equivalents of N($\alpha$)-carbobenzoxy-N($\phi$)-nitro-L-arginine and 1.6 equivalents of 1(3-dimethylamino-propyl)-3-ethyl carbodiimide (DCC) hydrochloride in alcohol:dioxane (1:1 v/v) was added portion wise (about 8–12 portions during 24–36 hours) and the reaction was allowed to proceed for an additional two days at pH 9–10 by adding sodium bicarbonate solution. The progress of the reaction was monitored by silica gel plate TLC using chloroform:methanol:water (1:1:0.5 v/v) as running buffer. After completion of the reaction, the solvents were evaporated in vacuo and the residue was washed twice with water followed by 0.1 M sodium hydroxide solution and again with water repeatedly to remove any trace of the free aminoglycoside, unreacted arginine and carbodiimide. The obtained precipitate was treated with a mixture of 0.5 equivalents of N($\alpha$)-carbobenzoxy-N($\phi$)-nitro-L-arginine and 0.6 equivalents of DCC for each amino group of the aminoglycoside in dioxane-chloroform mixture (1:1 v/v) and stirred at room temperature for 6 hours. The solvents were evaporated and the precipitate was dissolved in minimum amount of warm alcohol (40° C.) and cooled to room temperature, diethyl ether was added to the alcoholic solution until a gentle cloudiness was formed, the mixture was cooled at 0–4° C. The obtained colorless product was hydrogenated at atmospheric pressure in alcohol:dioxane:water (1:1:1 v/v) with acetic acid (3 ml) and Pd/C for 12 hours. After removal of Pd/C by filtration, a fresh portion of Pd/C was added and hydrogenation was continued for another 6 hours. Pd/C was filtered off, the solvents were evaporated in vacuo and the aminoglycoside-arginine conjugate was neutralized with acetic acid, precipitated as white solid by alcohol:dioxane (1:1 v/v) and dried. The aminoglycoside multi-arginine conjugates were analyzed by $^1$H NMR (in $D_2O$) and mass spectroscopy.

Experimental Results

Synthesis of site-specific arginine-aminoglycoside conjugations ($R_1$ and $R_6$) of Neomicin, Paromomycin and Neamine—FIG. 1 summarizes the various steps of the synthesis. Protection of all the aminoglycoside amines by Boc-anhydride [see FIG. 1, step (a)] was followed by protection of hydroxyl groups by benzyl bromide in anhydrous DMF [FIG. 1, step (b)]. The Boc groups were removed by trifluoroacetic acid [FIG. 1, step (c)], whereas the methylamino groups (see $R_1$, $R_6$ in FIG. 2) were protected by trityl chloride (Krakowiak, K. E. and Bradshaw, J. S. 1998. Synthetic Commun. 28; 3451–5432) [FIG. 1, step (d)]. All the amine groups were protected again by using Boc-anhydride [FIG. 1, step (e)]. Noteworthy that the selectivity of N-tritylation has been achieved due to the bulkiness of the trityl group, which attacks the methylamino groups ($R_1$ and/or $R_6$) rather than the other amino groups, while Boc-anhydride does not discriminate between methylamino and amino groups of the aminoglycosides. The selection of a trityl group for protection was also preferable for the detritylation process in very mild conditions by ytterbium triflate (Lu, R. J. et al., 2000. Tetrahedron Lett. 41: 2817–2819), without affecting the other protected amines and hydroxyls [FIG. 1, step (f)]. This procedure enabled the conjugation of arginine derivative to the methylamine groups while all the other amines and hydroxy groups remained 'protected' [FIG. 1, step (g)]. Finally, the protective groups were removed by catalytic hydrogenation and purification (FIG. 1, steps (h, i)].

Example 2

$^1$H NMR and Mass Spectra Analyses of the AACS of the Present Invention

The number of arginines conjugated to the different aminoglycosides was derived from the $^1$H NMR integration ratios of specific aminoglycoside protons versus the conjugated arginine protons, and mass spectroscopy confirmed their structure, as follows.

Experimental Procedures $^1$H NMR spectrum analysis—Intermediate and final products were analyzed by the Bruker AMX-400 (400 MHz) NMR Spectrophotometer at ambient temperature.

Mass spectrum analysis—Mass spectra were recorded using Micromass Platform LCZ 4000-Electro Spray Ionization (ESI) mode and MALDI-TOF MS.

Experimental Results

Paromomycin mono-arginine conjugate (ParomR1)—ParomR1 was prepared according to the general procedure I described in FIG. 1 and Example 1, hereinabove, using paromomycin free base as a precursor. Trityl chloride (1.5 equiv) was used to protect methylamino groups, N($\alpha$)-carbobenzoxy-N($\omega$)-nitro-L-arginine (1.5 equiv) and DCC (2 equiv) were used for the preparation of mono-arginine conjugate. ParomR1 (Yield: 59%) was analyzed by $^1$H NMR in $D_2O$ and by mass spectroscopy ESI.

$^1$H NMR (400 MHz) $\delta$ of the paromomycin moiety: 5.70 (1H, d, H-1'), 5.28 (1H, d, H-1''), 5.20 (1H, d, H-1'''), 2.35 (1H, dt, H-2e), 1.09 (1H, q, H-2a), and of the arginine moiety: 4.12 (1H, t, $H_\alpha$), 1.77 (2H, dt, $H_\beta$), 1.57 (2H, m, $H_\gamma$), 3.38 (2H, t, $H_\delta$). ESI m/z for mono-arginine-paromomycin (ParomR1) 771.77 calculated 771 (the calculated values are for the free base arginine-aminoglycoside conjugates).

Neomycin mono-arginine conjugate (NeoR1)—NeoR1 was prepared according to the general procedure I described in FIG. 1 and Example 1, hereinabove, using neomycin free base as aminoglycoside precursor. Trityl chloride (1.5 equiv.), N($\alpha$)-carbobenzoxy-N($\omega$)-nitro-L-arginine (1.5 equiv) and DCC (2 equiv) were used. NeoR1 (Yield: 61%) was confirmed by $^1$H NMR in ($D_2O$) and by mass spectroscopy ESI.

$^1$H NMR $\delta$ of the neomycin moiety: 5.92 (1H, d, H-1'), 5.33 (1H, d, H-1''), 5.20 (1H, d, H-1'''), 2.35 (1H, dt, H-2e), 1.12 (1H, q, H-2a), and of the arginine moiety: 4.12 (1H, t, $H_\alpha$), 1.77 (2H, dt, $H_\beta$), 1.57 (2H, m, $H_\gamma$), 3.32 (2H, t, $H_\delta$). Mass spectroscopy ESI m/z found for mono-arginine conjugate of neomycin (NeoR1) 770.86 calculated 771, (M+1) 771.83.

Neomycin di-arginine conjugate (NeoR2)—NeoR2 was prepared according to the general procedure I described in FIG. 1 and Example 1, hereinabove, using neomycin free base as aminoglycoside precursor. Trityl chloride (3 equiv.), N($\alpha$)-carbobenzoxy-N($\omega$)-nitro-L-arginine (3 equiv) and DCC (4 equiv) were used. NeoR2 (Yield: 60%) was characterized by $^1$H NMR in ($D_2O$) and by MALDI TOF mass spectroscopy.

$^1$H NMR $\delta$ of the neomycin moiety: 5.92 (1H, d, H-1'), 5.33 (1H, d, H-1''), 5.20 (1H, d, H-1'''), 2.35 (1H, dt, H-2e), 1.12 (1H, q, H-2a), and of the arginine moiety: 4.12 (2H, t, $H_\alpha$), 1.77 (4H, dt, $H_\beta$), 1.57 (4H, m, $H_\gamma$), 3.38 (4H, t, $H_\delta$). MALDI TOF MS m/z for di-arginine (NeoR2) 925.518, calculated 925.

Neamine mono-arginine conjugate (NeamR1)—NeamR1 was prepared according to the general procedure I described in FIG. 1 and Example 1, hereinabove, using neamine free base as aminoglycoside precursor. Trityl chloride (1.5 equiv), N($\alpha$)-carbobenzoxy-N($\omega$)-nitro-L-arginine (1.5 equiv.) and DCC (2 equiv) were used. NeamR1 (Yield: 51%) was analyzed by $^1$H NMR in ($D_2O$) and by mass spectroscopy ESI.

$^1$H NMR $\delta$ of the neamine moiety: 5.79 (1H, d, H-1'), 3.87–3.93 (3H, m, H-5, H-5' and H-3'), 3.42–3.48 (1H, m, H-1), 3.36 (1H, m, H-1'), 3.15 (1H, ddd, H-3), 2.39 (1H, ddd, H-2$_{eq}$), 1.55 (1H, ddd, H-2$_{ax}$) and of the arginine moiety: 4.02 (1H, t, $H_\alpha$), 1.7–1.8 (4H, m, $H_\beta$ and $H_\gamma$), 3.38 (2H, t, $H_\delta$). ESI m/z for mono-arginine-neamine (NeamR1) 479.79, calculated 479.

Paromomycin penta-arginine conjugate (ParomR5)—ParomR5 was prepared according to general procedure II which is described in Example 1, hereinabove, using paromomycin free base as a precursor. N($\alpha$)-carbobenzoxy-N($\omega$)-nitro-L-arginine (2 equiv), 1-(3-dimethyl-aminopropyl)-3-ethyl carbodiimide hydrochloride (1.6 equiv) and DCC (0.6 equiv) for each amino group of the aminoglycoside were used for arginine conjugation. ParomR5 (Yield: 52%) was analyzed by $^1$H NMR in ($D_2O$) and by MALDI TOF mass spectroscopy m/z found 1395.32, calculated 1395.

$^1$H NMR $\delta$ of the paromomycin moiety: 5.73 (1H, d, H-1'), 5.24 (1H, d, H-1''), 4.99 (1H, d, H-1'''), 1.78 (1H, dt, H-2e), 1.05 (1H, q, H-2a) and of the arginine moiety: 4.18 (5H, broad, $H_\alpha$), 1.78 (10H, br, $H_\beta$), 1.58 (10H, br, $H_\gamma$), 3.39 (10H, br, $H_\delta$).

Neomycin hexa-arginine conjugate (NeoR6)—NeoR6 was prepared essentially as reported for NeoR (Litovchick, A. et al., 2001. Biochemistry 40: 15612–15623) with small modification according to general procedure II which is described in Example 1, hereinabove. N($\alpha$)-carbobenzoxy-N($\omega$)-nitro-L-arginine (2 equiv), 1-(3-dimethylamino propyl)-3-ethyl carbodiimide hydrochloride (1.6 equiv) for each amino group of the aminoglycoside were used for arginine conjugation afforded product NeoR6 (yield: 53%) was analyzed by $^1$H NMR in $D_2O$ and MALDI TOF mass spectroscopy found m/z 1552.87 calculated 1552.

$^1$H NMR $\delta$ of the neomycin moiety: 5.91 (1H, d, H-1'), 5.33 (1H, d, H-1''), 5.20 (1H, d, H-1'''), 2.36 (1H, dt, H-2e), 1.12 (1H, q, H-2a), and of the arginine moiety: 4.12 (6H, br, $H_\alpha$), 1.76 (12H, br, $H_\beta$), 1.56 (12H, br, $H_\gamma$), 3.34 (12H, br, $H_\delta$).

Neamine tetra-arginine conjugate (NeamR4)—NeamR4 was prepared according to general procedure II which is described in Example 1, hereinabove, using neamine free base as a precursor. N($\alpha$)-carbobenzoxy-N($\omega$)-nitro-L-arginine (2 equiv), 1-(3-dimethylaminopropyi)-3-ethyl carodiimide hydrochloride (1.6 equiv) for each amino group of the aminoglycoside were used for arginine conjugation. NeamR4 (Yield: 57%) was analyzed by $^1$H NMR in $D_2O$ and by MALDI TOF mass spectroscopy found m/z 946.33 calculated 946.

$^1$H NMR $\delta$ of the neamine moiety: 5.48 (1H, d, H-1'), 3.72–3.80 (3H, m, H-5, H-5' and H-3'), 3.45–3.52 (1H, m, H-1), 3.36 (1H, m, H-1'), 3.28 (1H, ddd, H-3), 2.18 (1H, ddd, H-2$_{eq}$), 1.56 (1H, ddd, H-2$_{ax}$), and the arginine moiety: 3.95 (4H, br, $H_\alpha$), 1.5–1.6 (16H, br, $H_\beta$ and $H_\gamma$), 3.34 (8H, br, $H_\delta$).

Example 3

Binding of REVRH Peptide and Aminoglycoside-Arginine Conjugates (AAC) to RRE IIB and TAR RNA Background The molecular basis of Rev—Rev responsive element (RRE) recognition requires the interaction of the 17-mer arginine-rich Rev 33–50 peptide with a bulge portion of RRE IIB RNA [Kjems (1992) EMBO J. 11:1119–29]. RRE IIB contains an A-form RNA duplex with a 5-nucleotide bulge of unpaired nucleotides. Non-Watson-Crick pairs G·A and G·G are essential for Rev recognition [Bartel (1991) Cell 67: 529–36, and FIGS. 3a–c)]. NMR structure of Rev peptide RRE IIB complex reveals an $\alpha$-helical Rev peptide bound in the widened major groove of the RNA to the site formed by G·A and G·G base pairs (PDB access code 1ETF, 1ETG, Battiste, 1996. Science 273, 1547–1551).

The molecular basis of Tat-TAR interaction is the binding of 9-mer arginine-rich Tat peptide (residues 49–57) to a major groove of TAR RNA hairpin in the UCU bulge region [Aboul-Ela, F., Karn, J., and Varani, G. (1995). The structure of the human immunodeficiency virus Type 1 TAR RNA reveals principles of RNA recognition by Tat protein. J. Mol.

Biol. 253, 313–332; Brodsky, A. S., and Williamson, J. R. (1997). Solution structure of the HIV-2 TAR-argininamide complex. J. Mol. Biol. 267, 624–639; Long, K. S., and Crothers, D. M. (1999). Characterization of the solution conformations of unbound and Tat peptide-bound forms of HIV-1 TAR RNA. Biochemistry 38, 10059–10069]. Peptides carrying an arginine-rich sequence from Tat and even nona-arginine peptide bind to TAR RNA at the UCU bulge with high affinity and specificity [e.g. Calnan, B. J. Tidor, B., Biancalana, S., Hudson, D., and Frankel, A. D. (1991). Arginine-Mediated RNA Recognition: the Arginine Fork. Science 252, 1167–1171 (Published Erratum Appears In Science 1992, 255: 665); Weeks, K. M., Ampe, C., Schultz, S. C., Steitz, T. A. and D. M. Crothers. (1990). Fragments of the HIV-1 Tat Protein Specifically Bind TAR RNA, Science 249, 1281–1285]. Importantly, it was shown that not only Tat peptide binds TAR RNA with high affinity, but also Rev peptide does, moreover, functionally substituting Tat [Calnan Supra; Delling, U., Roy, S., Summer-Smith, M., Barnett, R., Reid, L., Rosen, C. A., and Sonenberg, N. (1991). The number of positively charged amino acids in the basic domain of Tat is critical for trans-activation and complex formation with TAR RNA. Proc. Natl. Acad. Sci. USA 88, 6234–8].

The structure-function relationship of AACs with respect of RNA binding is an important issue towards drug development. The present inventors have hypothesized that similar to the recognition of 16S RNA by rings I and II of neomycin B class of antibiotics e.g., neamine and paromomycin (Fourmy, D. et al., 1998. J. Mol. Biol. 277: 347–362), being conjugated to arginine would be sufficient to mediate specific interactions with the HIV-1 RNAs. Thus, the present inventors have tested the binding affinities of site-specific mono-arginine conjugates of neamine, paromomycin and neomycin B, as well as tetra-arginine neamine, penta-arginine paromomycin, di- and hexa-arginine neomycin B conjugates to HIV-1 TAR and RRE RNAs, as follows.

Experimental Procedures

Preparation of TAR and RRE IIB RNAs—TAR and RRE IIB RNAs were purchased from Dharmacon Co. and were deprotected according to manufacturer's instructions. The concentrations of RNA oligonucleotides were determined spectrophotometrically by absorption at 260 nm.

Rhodamine Rev Peptide (RhdRev)—RhdRev [Wang (1997) Biochemistry 36:768–779] was prepared from Rev peptide by reacting it with carboxytetramethyl rhodamine succinimide (Molecular probes, Inc. Eugene, Oreg., USA). RhdRev was HPLC purified on a 250×4.6 mm reverse phase column (C18, YMC-18 AQ) and was analyzed by mass-spectroscopy (MALDI-TOF MS). RhdRev concentration was determined spectrophotometrically at 550 nm using a molar extinction coefficient of $6.00 \times 10^4$ M$^{-1}$cm$^{-1}$ previously described [Wang (1997) Biochemistry 36:768–779].

Fluorescence Measurements—Fluorescence anisotropy measurements were performed as previously described for NeoR6 [Litovchick (2001) Biochemistry 40:15612–15623; Hamasaki, K. and Ueno, A. 2001. Bioorg. Med. Chem. Lett. 11: 591–594; Lacourciere, K. A. et al., 2000. Biochemistry 39: 5630–5641; Wang, Y. et al., 1997. Biochemistry 36: 768–779]. The fluorescent tracer solution was excited at 550 nm and monitored at 580 nm. The integration time was 5 s. For every point, 6 to 10 measurements were taken, and their average values were used for calculation. Measurements were carried out in a buffer solution containing 85 mM NaCl, 2 mM KCl, 0.5 mM CaCl$_2$, 0.5 mM MgCl$_2$, and 10 mM HEPES (pH 7.5). Prior to measurements, RNA constructs were renatured by incubation in the binding buffer for 3 min at 90° C. followed by cooling to 25° C. Equation 1 $(A=A_0+A\{[RNA]_0+[tracer]_0+K_d-[([RNA]_0+[tracer]_0+K_d)^2-4[RNA]_0[tracer]_0]^{1/2}\}/2)$ was used for the determination of the dissociation constant ($K_d$) for the interactions of the RNA and a fluorescent tracer, such as RhdRev, wherein "A" and "$A_0$" in equation 1 are the fluorescence anisotropy of the fluorescent tracer in the presence and absence of RNA, respectively, and "·A" is the difference between the fluorescence anisotropy of the tracer at extrapolated infinite concentration of RNA minus the fluorescence anisotropy in the absence of RNA. [RNA]$_0$ and [tracer]$_0$ are the initial concentrations of RNA and the fluorescent tracer (RhdRev), respectively.

Equation 2 $([AAC]_0=[K_D(A_\infty-A)/K_d(A-A_0)+1][[RNA]_0-K_d(A-A_0)/(A_\infty-A)-[tracer]_0(A-A_0)/(A_\infty-A)])$ was used for the calculation of the $K_D$ values in the competition-binding assay, wherein "$K_D$" in equation 2 is the dissociation constant between the RNA and the AAC, [AAC]$_0$ is the initial concentration of the aminoglycoside-arginine conjugates. Both $K_d$ and $K_D$ were determined by non-linear curve fitting using the equations described above and in Wang Y, et al., (Biochemistry 36:768–779, 1997), and are presented as mean values of three independent measurements. The IC$_{50}$ values, i.e. concentrations of AACs, which cause 50% inhibition of the fluorescent tracer binding to the corresponding RNA were determined by a simple competitive binding model [Chapman (2002) Antiviral Research 54:149–162].

Experimental Results

RhdRev has a high binding affinity to TAR—Rev peptide labeled with carboxymethyl rhodamine (RhdRev) was used as a fluorescent probe for both TAR and RRE IIB RNA constructs. In order to address binding of the RhdRev peptide to the RRE IIB and TAR, 10 nM of the fluorescent tracer were titrated with TAR or RRE IIB RNA solutions and the anisotropy values were recorded. Using non-linear curve fitting, the dissociation constants of RhdRev to TAR and RRE IIB at 85 mM NaCl were determined. The binding isotherms for the RhdRev to RRE IIB and TAR are shown in FIGS. 4a–b. The corresponding dissociation constants, measured for RRE IIB and for TAR were $K_D$=16 nM and $K_D$=7 nM, respectively. The high binding affinity of RhdRev to TAR is in agreement with the finding that Rev peptide binds TAR and functionally substitute Tat (Calnan, B. J. et al., 1991. Science 252: 1167–1171; Delling, U. et al., 1991. Proc. Natl. Acad. Sci. USA 88: 6234–8).

AACs with several arginine side chains efficiently competed with RhdRevfor TAR RNA binding—The AACs of the present invention (shown in FIG. 2) were tested as competitive inhibitors for RhdRev binding to TAR and RRE constructs. FIGS. 5a–f demonstrate the binding of AACs to TAR and RRE IIB RNA constructs as determined by a fluorescence anisotropy competition assay. Briefly, 10 nM of the RhdRev fluorescent tracer were mixed with 20 nM TAR or RRE IIB RNA. Tracer—RNA complexes were further titrated with AAC solutions and anisotropy values were recorded. Using nonlinear curve fitting, the dissociation constants ($K_D$) of AACs-TAR and AACs-RRE IIB RNA at 85 mM NaCl were determined and shown in Table 2, below.

TABLE 2

| Compound | $K_D$TAR/RhdRev[a] | $IC_{50}$TAR/RhdRev[b] | $K_D$ RRE IIB[c] | $IC_{50}$ RRE IIB[d] |
|---|---|---|---|---|
| RhdRev[e] | 7.3 ± 0.5 | — | 16.6 ± 2.7 | — |
| NeoR6 | 5.0 ± 0.2 | 19.9 ± 2.7 | 23.3 ± 0.95 | 72.7 ± 10.1 |
| NeoR2 | >500[f] | >500[f] | 111.5 ± 3.7 | 207.9 ± 21.1 |
| NeoR1 | >500[f] | >500[f] | 200.2 ± 5.9 | 352.8 ± 31.9 |
| ParomR5 | 15.1 ± 0.4 | 34.3 ± 5.7 | 95.9 ± 2.2 | 149.4 ± 12.3 |
| ParomR1 | >500[f] | >500[f] | 254.2 ± 7.8 | 406.8 ± 41.0 |
| NeamR4 | 30.1 ± 1.2 | 82.8 ± 7.7 | 54.7 ± 1.1 | 118.8 ± 13.5 |
| NeamR1 | >500[f] | >500[f] | 233.4 ± 4.5 | 342.4 ± 29.5 |

[a]$K_D$ and [b]$IC_{50}$ determined as competition of AACs with RhdRev for TAR RNA binding;
[c]$K_D$ and [d]$IC_{50}$ determined as competition of AACs with RhdRev for RRE IIB RNA binding;
[e]measured as a direct binding of RhdRev to TAR and RRE IIB RINA;
[f]20 μM of mono and di-arginine aminoglycoside derivatives failed to completely expel RhdRev from the complex with TAR, thus $IC_{50}$'s and $K_D$'s are >500 nM and could not be accurately determined.

As can be seen from Table 2 hereinabove, the examined AACs competed with RhdRev for RRE IIB binding. However, when similar competition experiments were performed in the presence of TAR RNA and RhdRev, only AACs with several arginine side chains, NeoR6, essentially, ParomR5 and NeamR4 efficiently competed with RhdRev for TAR RNA binding (FIGS. 5a–f, Table 2). Interestingly, AACs, with only one or two arginine side chains failed to completely expel the tracer from the TAR complex preventing anisotropy to return to its initial value, thereby rendering affinity determination impossible in these cases. Note that binding affinities of NeoR6, ParomR5 and NeamR4 for TAR are greater than for RRE IIB (Table 2).

The results presented herein indicate that NeoR6 binds with the highest affinity to both RRE IIB ($K_D$ 23 nM) and TAR ($K_D$ 5 nM) (FIGS. 5a–b and Table 2), which affinity is comparable to the respective natural ligands, $Rev_{34-50}$ (40 nM) and $Tat_{49-57}$ (12 nM). ParomR5 bound TAR with a $K_D$ value 15 nM, essentially three times weaker than NeoR6, while binding of ParomR5 to RRE IIB exhibited a $K_D$ of 96 nM which was about 4 times weaker than NeoR6 (FIGS. 5c–d). As shown in FIGS. 5e–f, NeamR4 bound TAR with $K_D$ value of 30 nM, 6 times weaker than NeoR6, while a $K_D$ of 55 nM characterized the binding of NeamR4 to RRE IIB, only by times weaker than NeoR6 (Table 2). Thus, NeamR4 binds RRE IIB more efficiently than ParomR5.

Altogether, these results demonstrate that AACs with several arginines clearly bind TAR better than RRE IIB. Note that the $IC_{50}$ values for AACs competition with RhdRev for TAR and RRE IIB binding were also determined for comparison with published data (Chapman, 2002. Antiviral Research, 54: 149–162; Hamasaki, K. and Ueno, A. 2001. Bioorg. Med. Chem. Lett. 11: 591–594), although the $IC_{50}$ values are less accurate than the $K_D$ values (Table 2).

The conjugation of arginine to the methylamino group (R1) of ring I of aminoglycoside is important for RRE binding—To illustrate the dependence of the affinity of various AACs to RNA, the $K_D$ values of their RRE IIB binding versus the number of arginine side chains and number of rings in the aminoglycoside core was plotted. As is shown in FIG. 6, NeoR6 displayed the highest affinity to RRE IIB (i.e. the lowest $K_D$ value) as expected from an AAC with a high number of rings (i.e., 4 rings) and a high number of arginine moieties. However, there was not much difference in the affinity of NeamR4 (having 2 rings) and ParomR5 (having 4 rings). On the contary, NeamR4 exhibited even lower $K_D$ value (higher affinity) than ParomR5. Thus, not only are the number of rings and arginine moieties essential for efficient RNA binding, but also the conjugation of arginine to the methylamino group (R1) of ring I of aminoglycoside is very important for binding to RRE. While NeamR4 plays a role of a minimal RNA recognition unit [Fourmy (1998) J. Mol. Biol. 277, 347–362], arginine-conjugated rings I and II are not sufficient for effective RNA binding. Thus, NeamR4 is still a significantly weaker RNA binder than NeoR6, suggesting that rings III and IV and increase number of arginine moieties lead to higher affinity and specificity of AACs-RRE and TAR RNA binding.

Summary—The hexa-arginine neomycin B conjugate reveals the highest binding affinity either to TAR or RRE IIB. AACs with several arginine groups bind TAR better than RRE IIB. The mono- and di-arginine conjgtes of the aminoglycosides bind RRE IIB and TAR significantly less efficient than the per-arginine derivatives.

Analysis and Discussion—Fluorescence anisotropy measurements of aminoglycoside binding to RRE IIB using fluorescein-$Rev_{34-50}$ as a fluorescent tracer, revealed dissociation constants in the range of μM. Among the aminoglycosides, neomycin B binds with the highest affinity with $K_D$ of 1.18 μM (Hamasaki, K. and Ueno, A. 2001. Bioorg. Med. Chem. Lett. 11: 591–594; Lacourciere, K. A. et. al., 2000. Biochemistry 39: 5630–5641), ~550 times weaker than NeoR6 binding to RRE IIB and by 6 and 7 times weaker than NeoR1 and NeoR2, respectively, indicating that even one arginine conjugated to neomycin B significantly increases the binding affinity to HIV-1 RNAs.

In contrast, guanidino derivatives of aminoglycosides (Luedtke, N. S. et al., 2000. J. Am. Soc. 122: 12035–12036; Baker, T. J. et al., 2000. J. Org. Chem. Soc. 122: 9054–9058) or even y-guanidino attached to the aminoglycosides via a linker, such as guanidino butirate conjugated to aminoglycoside (kanamycine A conjugated to four γ-guadinno butiric acid, GB4K) (Litovchick, A. et al., 2000. Biochemistry 39: 2838–2852) bind TAR or RRE RNAs with a very low affinity. Similarly, their anti HIV-1 activity is very low in comparison to the respective arginine derivatives (Lapidot, A. and Litovchick, A. 2000. Drug Development Research 50: 502–515; Litovchick, A. et al., 2001. Biochemistry 40: 15612–15623; Cabrera, C. et al., 2000. AIDS Res. Hum. Retroviruses 16: 627–634). The footprinting analysis presented in Litovchick, A. et al., 2000 (Biochemistry 39: 2838–2852) demonstrate that GB4K cannot protect the bulge region of TAR from RNase A cleavage in contrast to Tat peptide (R52) or AACs. Thus, the α-amino group of arginine plays an important role in binding to TAR and in an anti HIV-1 activity.

One of the possible explanations for AACs binding behavior to TAR and RRE IIB is that AACs bear features of both aminoglycosides and peptides [Litovchick (2000) Biochemistry,39: 2838–2852]. It was shown that neomycin B binds RRE IIB in the major groove, at the lower stem-bulge region of the construct, close to the Rev peptide binding site (Lacourciere, 2000. Biochemistry 39: 5630–5641), whereas neomycin B binds TAR in the minor groove, also in the lower stem-bulge region of TAR to a region very different from the Tat binding site (Faber, 2000. 275: 20660–6); both TAR and RRE bind peptides in the major groove. Since the natural peptide ligand and AACs would anyway bind to RRE in the same groove region, it is probable that the exact nature of AAC-RNA interaction in the case of RRE IIB is less crucial than in the case of TAR. Thus, it is likely that only AACs with high arginine substitution (e.g. NeoR6, ParomR5 or NeamR4), which actually mimic the peptides, bind in the peptide-binding site on TAR and thus efficiently compete with the peptide probe.

Several structural studies of free and ligated RRE-IIB have been published in he past few years Peterson, R. D. and Feigon, J. I. 1996. J. Mol. Biol. 264: 863–877; Hunb, L. W. et al., 2000. Proc. Natl. Acad. Sci. USA 97: 5107–5112; Ippolito, J. A. and Steitz, T. A. 1999. J. Mol. Biol. 295: 711–717; Zhang, Q. et al., 2001. Chemistry and Biology. 8: 511–520; Gosser. Y. et al., 2001. Nature Structural Biology 8: 146–150; Battiste, J. L. et al., 1996. Science 273: 1547–1551). It was found that the stem-loop RRE-IIB changes conformation upon binding of Rev [Hunb (2000), Supra; Battiste (1996) Supra]. Moreover, it appears that the free RRE-IIB is rather flexible having different conformation in solution and in the crystal [Ippolito (1999), Supra]. In contrast, when RRE-IIB is bound to a peptide its conformation stabilizes [Zhang (2001) Supra; Gosser (2001), Supra]. Based on the available structures and on the fact that NeoR6 competes with Rev, assuming for the same binding site or induce conformational changes in the RRE-IIB stem-loop region similarly to that of Rev, it is anticipated that the interactions of arginine moieties of NeoR6 are likely to imitate at least in part the interactions of the arginine side chains of Rev with RRE.

The experimental results presented herein suggest that the arginine moieties at position $R_1$ on ring I, and $R_3$ and $R_4$ on ring II (FIG. 2) are important for binding. The important contribution of arginine at position $R_1$ is demonstrated by the lower affinity of ParomR5 to RRE IIB compared to NeamR4. Thus, even though ParomR5 consists of 4 rings and 5 arginine moieties it lacks arginine at position $R_1$ (Table 2, hereinabove and FIG. 2), which is probably the reason for the lower affinity. The most potent binder, NeoR6, forms additional arginine-RRE interactions compared to NeamR4 (FIG. 6). These observations are also in accordance with the differences in arginine side chain dynamics of Rev-RRE complex (Wilkinson, T. A. et al., 2000. Chem. and Biol. 9: 185–193).

Example 4

Anti-HIV Activity of Aminoglycoside-Arginine Conjugates

Materials and Experimental Methods

Synthesis of Aminoglycoside-Arginine Conjugates—See Examples 1–2.

Cell culture and Inhibition of HIV-1 infection—Peripheral blood mononuclear cells (PBMC), PM1, MT2, and H9 (lymphocyte cell lines permissive to T-tropic HIV-1 isolates), U38 (a macrophage cell line permissive to M-tropic HIV-1 isolates), cMAGI [cMAGI cell line is permissive to both M and T tropic HIV-1 isolates as well as to primary and laboratory adopted HIV-1 isolates, Chackerian (1997) J Virol. 71, 3932–3939; Collins (2000) Nat. Med. 6, 475–479], and H9+ (H9 cells chronically infected with HIV-1$_{IIIB}$) cell lines were cultured in RPMI 1640 medium (GibcoBRL, Life Technologies, Paisley, UK) containing 10% fetal calf serum (FCS) and antibiotics. T-tropic HIV-1 isolates were propagated by subculture in MT2 as previously described [Litovchick (2001) Biochemistry 40, 15612–15623]. Aliquots of cell-free culture supernatants were used as viral inoculum. The indicated AACs were dissolved in the RPMI 1640 medium. Cytotoxicity determinations were carried out in MT2 and H9 cells by trypan blue exclusion assay.

Viral inhibition was determined by incubating cMAGI HIV-1 reporter cells with 0.2–0.5 multiplicity of infection of HIV-1$_{IIIB}$ for 4 days at 37° C. in the presence or absence of various concentration of AACs, prior to counting the number of HIV-1 infected cells (stained blue). The cytopathic effects of the viral infection of MT2 cells were also analyzed by microscopic assessment of syncytium formation. These latter data were obtained by analysis of duplicate samples by two independent observers.

Viral binding assay—To measure the ability of AACs to inhibit viral binding to cells, HIV-1 viral particles were radioactively labeled by endogenous reverse transcription (ERT), as previously described [Borkow (1997) J. Virol. 71, 3023–3030]. Briefly, 0.5 ml of HIV-1 particles (1.5–5 ng of p24) were added to 0.5 ml of ERT reaction mixture (final concentrations: 10 mM Tris HCl, pH 8.0, 150 mM NaCl, 1 mM MgCl$_2$, 50 μM each dATP, dTTP, dCTP and dGTP, as well as 50 μCi of [α-$^{32}$P] dATP). After 2 h of incubation at 37° C. the reaction mixture was diluted with PBS to 2 mL, and the viral particles were concentrated to final volume of 50 μL using Centricon YM-50 centrifugal concentrator (Millipore, Bedford, Mass., USA), according to the manufacturer's directions. This procedure was repeated four times in order to remove unbound radiolabel. The viral particles were incubated for 2 h at 37° C. with 200,000 MT2 or U937 cells in 0.5 mL of RPMI/10% FCS in the presence of various concentrations of AACs. Following the incubation, the cells were washed twice with PBS by centrifugation at 400×g for 10 min. The pellets were resuspended in PBS and transferred onto glass-fiber filters (Millipore, Bedford, Mass., USA). The filters were washed twice with PBS, dried, and counted by a gamma-counter.

Experimental Results

Anti-HIV activity of AACs—The AACs described above inhibited a variety of HIV-1 isolates, including HIV-1$_{IIIB}$ laboratory adapted T-tropic isolate, clade C HIV-1 clinical isolate, as well as AZT, 3TC and UC781 resistant HIV-1$_{IIIB}$ strains, with no significant differences in the concentrations that caused 50% inhibition of viral production (EC$_{50}$ of 1.7–6.2 μM for the multi-arginine conjugates and >10 μM for the mono-arginine conjugates). In contrast, the aminoglycoside antibiotics: neamine, gentamicin, neomycin and paromomycin did not reveal antiviral activity up to 100 μM. The concentration of AACs that caused cytotoxicity in 50% of the cells (CC$_{50}$) was higher than 250 μM. The in vitro 50% therapeutic index (TI$_{50}$=ratio CC$_{50}$/EC$_{50}$) is therefore at least 40 for most AACs (data not shown).

As shown in FIGS. 7a–b the presence of R3G or NeoR6 could inhibit viral proliferation through viral infection, but more importantly through the first two hours of viral infection, indicating that the AACs of the present invention can inhibit the first stages of HIV-1 infectivity, and/or that the AACs are taken readily into the cells, and inhibit subsequent viral infectivity steps.

Effect of AACs on viral binding to cells—In order to test if the AACs of the present invention interfere with the binding of the virus to the cells, a competition of NeoR6 and R3G with the binding of $^{32}P$ labeled HIV-1 particles to MT2 cells (CD4+ T-lymphocytes) or to U937 cells (CD4+ monocytes).

As shown in FIGS. 8a–b, both compounds efficiently inhibited the binding of HIV-1$_{IIIB}$ to MT2 cells and the binding of HIV-1 clinical isolate lade C to U937 cells, in a dose-dependant manner.

Example 5

Uptake of Aminoglycoside-Arginine Conjugates by Human T Cells and NEOR6 Toxicity Test in Animal Model Materials and Experimental Procedures AAC Fluorescent Derivatives—Acetate anions of AACs were removed via ion exchange chromatography by AG-MP 1 (converted from Cl to OH form, 100–200 mesh) using water as an eluent. The collected eluent was evaporated to dryness using Speedvac concentrator. AACs fluorescent derivatives including NeoR1-FITC, NeoR2-FITC, NeoR6-FITC, NeamR1-FITC, NeamR4-FITC, ParomR1-FITC, ParomR5-FITC and R3G-FITC, were prepared by reacting AACs with fluoresceine isothiocyanate (FITC, Sigma, Rehovot, Israel) in a 1:1 molar ratio in water:methanol:dioxane (1:1:1 v/v) mixture for 1 hour at room temperature. Fluorescent conjugates were purified as previously described for NeoR6 [Litovchick (2001) Biochemistry 40, 15612–15623].

Cellular uptake using AAC fluorescent probes—U38, PM1, H9 cells and PBMC($10^5$) were incubated for 20 minutes at room temperature in 100 μl RPMI 1640 medium (Gibco-BRL, Life-Technologies, UK) including AAC-FITC derivatives as indicated at a final concentration of 0.5 μM. Cells were washed twice, resuspended in 100 μl medium and analyzed with a Zeiss Axiophot fluorescent microscope.

Cellular uptake competition of AACs with NeoR6-FITC—Phosphate-buffered saline (PBS) containing 0.5 μM NeoR6-FITC only or mixed with 10, 40 or 100 fold higher concentrations of non-labeled AACs, was added to $10^5$ MT-2 cells (50 μl final volume). After 5 or 15 min of incubation at room temperature, the cells were washed twice with ice-cold PBS and fixed in PBS containing 1% paraformaldehyde. The fluorescence was then analyzed by flow cytometry (FACScan, Becton Dickinson Imunocytometry Systems, San Jose, Calif., USA). For each sample 10,000 events were acquired. Data were analyzed and processed.

Preparation of NeoR6 for in vivo injections—Dosing solutions were freshly prepared on the day of dosing by dissolving the NeoR6 powder with sterile physiological saline to provide final concentrations of either 2.5 or 5 mg/ml. Injection volumes applied ranged from 4–10 ml/kg Administration of NeoR6 into mice—Male and female ICR (CD-1$^R$) mice (Harlan Laboratories Israel, Ltd) at the age of 4–5 weeks were intravenously injected into one of the tail veins with a single dose of 10, 15, 25, 30 or 35 mg/kg or with two successive intravenous (IV) injections (at a dose level of 25 mg/kg) interspaced by a 3-hour dosing interval as is shown in Table 3, hereinbelow.

TABLE 3

Constitution of treatment groups and weight gain during treatment

| Group No. | No. and sex of animals | Dose level (mg/kg) | Method of Injection | Weight Gain (gr.) (Day 1–15) |
|---|---|---|---|---|
| 1M | N = 2, Males | 10 | Single Bolus Injection | 5.3; 5.8 |
| 1F | N = 2, Females | 10 | | 4.1; 0 |
| 2F | N = 1, Female | 15 | | 4.3 |
| 3F | N = 1, female | 25 | | 5.3 |
| 4F | N = 2, Females | 30 | | 1.6; — |
| 5M | N = 2, Males | 35 | | 8.3; 7.1 |
| 6M | N = 3, Males | 50 (2 × 25) | Two injections at 3 hours dosing interval | 7.2; 7.2; 8.9 |
| 6F | N = 3, Females | 50 (2 × 25) | | 4.5; 2.4; 4.7 |

Observation of clinical signs post-NeoR6 injection—On the day of injection, careful clinical examinations were carried out continuously during the first 90 minutes post-injection. Thereafter, animals were inspected at least once a day for 14 consecutive days. Observations included changes in the skin and fur, eyes and mucous membranes, respiratory, circulatory, autonomic and central nervous systems, somato-motor activity and behavior pattern with particular attention to occurrence of tremors, convulsions, salivation, diarrhea, lethargy, sleep and coma.

Evaluation of weight gain during treatment—Individual body weights of animals were determined just prior to NeoR6 injection Surviving animals were weighed on Day 8 post injection and upon study termination prior to the scheduled sacrifice on Day 15.

Necropsy and Gross Pathology—All test animals, including decedents were subjected to gross necropsy. At necropsy all animals were thoroughly examined for abnormality of tissues or organs. All major body cavities were opened, larger organs were sectioned and the gastro-intestinal tract was opened at intervals for examination of the mucosal surfaces. The normal appearance of major organs was confirmed for each animal and any gross pathological changes or abnormalities were described.

Experimental Results

Cellular uptake of AACs—Fluorescent labeling studies have shown that R4K, R3G and NeoR6 accumulate in different cell types, including lymphocytes, PBMC and neurons [Litovchick (2000) Biochemistry 39:2838–2852; Litovchick (2000) Biochemistry 39, 2838–2852; Catani (2003) J. Neurochemistry 84:1237–1245].

Similarly, as shown in FIGS. 9a–f, ParomR5, NeamR4 and NeoR6 labeled with FITC were uptaken by PM1 cells following 10 minutes of incubation with the compositions. Interestingly, FITC-labeled mono- and di-arginine conjugates of neomycin B, mono-arginine-paromomycin and mono-arginine-neamine also penetrated and accumulate in less than 10 minutes of incubation in macrophages (U38) and lymphocytes (H9 and PM1 cells, data not shown). These results demonstrate that the AAC of the present invention are not toxic to a number of cell cultures when provided at a concentration of 500 μM.

In order to test specific uptake of the AACs of the present invention, a competition was effected between fluorescently-labeled NeoR6-FITC (0.5 μM) and excess of non-labeled AACs examining cellular uptake of the first using flow cytometry following 5 or 15 minutes of incubation with MT-2 cells. As shown in FIG. 10, at 100 fold excess of the non-labeled AACs, uptake of NeoR6-FITC was inhibited by ParomR5, NeamR4 and NeoR2 at about 50% less affinity than NeoR6. Interestingly, the mono-arginine derivatives of NeoR1, NeamR1 and ParomR1 did not compete with NeoR6-FITC. At 40 fold excess of AACs only ParomR5 inhibited cellular uptake of NeoR6-FITC at about 50% less efficient than NeoR6 (FIG. 10).

No toxicity of NeoR6 in mice—The potential acute toxicity of NeoR6 was assessed in male and female ICR mice which were infected with a single dose of 10, 15, 25, 30 or 35 mg/kg or with two successive intravenous (IV) injections (at a dose level of 25 mg/kg) interspaced by a 3-hour dosing interval. No obvious reaction to treatment was evident after the single intravenous administration of NeoR6 at the doses of 10, 15 and 25 mg/kg. At 30 and 35 mg/kg, all of the clinical signs observed and consisting primarily of respiratory and motoric irregularities and were confined to the first 10 min after dosing. Thereafter, rapid recovery occurred and no other abnormalities were seen until termination of the study at 14 days post-administration. The only incidence of mortality noted was of a single female mouse which was injected with 30 mg/kg treatment and which died within the first five minutes post-injection. Dosing with 50 mg/kg administered as 2 successive injections with an interdosing interval of 3 hours, did not cause any adverse effects other than a very transient reduction in respiratory rate and spontaneous motor activity seen within 1–2 min post-injection.

Normal weight gain and absence of pathological findings in NeoR6 treated mice—All injected mice, with the exception of 2 females (which were injected with 10 or 30 mg/kg) displayed a normal mode of weight gain within the entire 14-day observation period (Table 3, hereinabove). In addition, no pathological findings were neither noted in the decedent of the treated animals nor in the surviving animals.

Thus, these results demonstrate that the maximum tolerated dose (MTD) level for acute IV administered NeoR6 is within the range of 30 to 35 mg/kg. In addition, these results indicate that subdivision of the total treatment dose into two portions and administration at an inter-dosing interval of 3 hours would significantly increase the MTD level of NeoR6.

Example 6

Inhibition of Anti-CXCR4 MAB Binding to Cells by AACS

Materials and Experimental Procedures

Interaction of AACs with CXCR4 was determined by flow cytometry (FACScan, Becton Dickinson) as described recently (Litovchick et al., 2001, supra). Briefly, $0.5 \times 10^6$ cells were washed in ice-cold PBS containing 0.1% sodium azide (wash buffer) and incubated at 4° C. with anti-CXCR4 mAb, 12G5 (PharMingen, San Diego, Calif.) conjugated to phycoerithrine (PE), in the absence or presence of different concentrations of the AACs. After 30 min of incubation, the cells were washed with ice-cold wash buffer and fixed in PBS containing 1% paraformaldehyde. Non-specific fluorescence was assessed by using isotype-matched control. For each sample 10,000 events were acquired. Data were analyzed and processed using CellQuest™ software (Becton Dickinson).

Experimental Results

Inhibition of anti-CXCR4 mAb binding to cells by AACs—The inhibition of T-tropic HIV-1 isolates binding to cells, together with previous observations, showing that NeoR6 and R3G interact with CXCR4, but not with CD4 or CCR5 [Cabrera (2002) Antiviral Res. 53, 1–8; Litovchick et al., 2001, Supra; Cabrera (2000) AIDS Res. Hum. Retroviruses 16, 627–634] prompted further examination of AAC binding to CXCR4. The ability of various AACs to block the binding of PE labeled 12G5 mAb to CXCR4 in PM1 cells and in PBMC was investigated.

As shown in one representative experiment shown in FIGS. 11a–d, 10 µM of NeoR6 and R3G reduced the binding of the mAb to the cells by 90% and 84%, respectively [from a median fluorescence intensity (MFI) of 451 to 76 and 89, respectively, while the MFI of the isotype control was 30]. Ten µM of ParomR5, NeamR4, NeoR1, and NeoR2 reduced 12G5 mAb binding by 81%, 60%, 50% and 48%, respectively, while ParomR1 and NeamR1 reduced 12G5 mAb binding only by 16% and 5%, respectively. As expected aminoglycoside antibiotics (i.e., 20 µM of neomycin, paromomycin and neamine) did not inhibit 12G5 mAb binding to the cell coreceptor CXCR4 (data not shown).

Example 7

Inhibition of FITC-Labeled AAC Uptake By Stromal Cells—Derived Factor 1α (SDF-1α)

Materials and Experimental Procedures

Competition between FITC labeled AACs and SDF-1α was effected as follows: FITC labeled AACs (1 µM) including NeoR6, NeamR4, ParomR5, NeoR1, NeoR2, NeamR1 and ParomR1 were incubated at 4° C. with $2 \times 10^5$ PM1, MT2 or PBMC, in the presence or absence of the indicated concentrations of SDF-1α (R&D Systems, Minneapolis, USA). Following 30 minutes of incubation, cells were washed with ice-cold wash buffer and analyzed by flow cytometry as described above.

Competition between FITC labelled AACs (1 mM) and RANTES (2.5 mM, Pepro Tech Inc., New Jersey, USA) was effected in $2 \times 10^5$ cMAGI cells. Following 30 min of incubation, cells were washed with ice-cold wash buffer and analysed by flow cytometry as described above.

Experimental Results

Inhibition of FITC-labeled AAC uptake by stromal cells—derived factor 1α (SDF-1α)—Cellular uptake of various AACs was addressed in the presence of SDF-1α, the sole ligand for CXCR-4. The ability of SDF-1α to inhibit binding of PE-labeled anti-CXCR4 mAb 12G5 to PM1 cells was used as a control. As shown in FIGS. 12a–h, 62.5 and 125 nM SDF-1α inhibited significantly the binding of the anti-CXCR4 mAB 12G5 to PM1 cells. Similar results were obtained when PBMC were used (data not shown). As shown, SDF-1α decreased NeoR6-FITC, ParomR5-FITC and NeamR4-FITC (1 µM each) cell uptake in a dose dependant manner. Furthermore, while 62.5 nM of SDF-1α caused minor inhibition of NeoR6 (~10%), 125 and 250 nM of SDF-1α inhibited by 30% and 40% cell uptake of NeoR6, respectively (i.e., from MFI of 61 to 54, 46 and 42, for 62.5, 125 and 250 nM SDF-1α, respectively, and a background MFI of 10). Noteworthy is that cell uptake inhibition by SDF-1α at concentration 125 nM of ParomR5 and NeamR4, were similar (i.e., about 50%; from MFI of 104 to 83, 59 and 53, for 62.5, 125 and 250 nM SDF-1α, respectively for ParomR5; and from a MFI of 96 to 56, 52 and 50, for 62.5, 125 and 250 nM SDF-1α, respectively- both with a background MFI of 10). No significant increased effects could be detected in the presence of the higher dose of SDF-1α (250 nM) or even in the presence of 1 µM SDF-1α (not shown). Similar effects were found by using MT2 cells (data not shown). In contrast, no effect of SDF-1α: on mono-, diarginine derivatives of neomycin or mono-arginine of paromomycin and neamine conjugates uptake, either by 250 nM or 1 µM of SDF-1α could be observed in PM1 or MT2 cells. It is worth noting that the anti-HIV-1 $EC_{50}$ of SDF-1α is ~70 fold lower than that of NeoR6, whereas the inhibition ($IC_{50}$) of 12G5 mAb binding to CXCR4 is only 2,6 times lower than of NeoR6 (Cabrera et al., 2002 Supra).

No inhibition of multi-arginines aminoglycoside conjugates cell uptake by CCR5 ligand RANTES—It will be appreciated that neither R3G nor R4K or NeoR6 inhibit the binding of 2D7, a mAb directed to CCR5 or of an anti CD4 antibody (Leu 3a) in PHA stimulated peripheral blood lymphocytes (PBL) (Litovchick et al., 2001; Cabrera et al., 2002). The results presented hereinabove show that 2.5 mM RANTES did not affect uptake of FITC derivatives of NeoR6, ParomR5 or NeamR4 by cMAGI cells (not shown), supporting previous studies implying that AACs do not interact with the HIV-1 coreceptor CCR5.

Example 8

GP120 Inhibits Cellular Uptake Of AACS

Materials and Experimental Procedures

Competition assay—Competition between FITC labeled AACs HIV-1 gp120 was effected as follows: FITC labeled AACs (1 μM) including NeoR6, NeamR4, ParomR5, NeoR1, NeoR2, NeamR1 and ParomR1 were incubated at 4° C. with 2×10⁵ PM1, MT2 or PBMC, in the presence or absence of 5 μM recombinant HIV-1$_{IIIB}$ gp120 (NIH AIDS Research & Reference Reagent Program). Following 30 minutes of incubation, cells were washed with ice-cold wash buffer and analyzed by flow cytometry as described above.

Experimental Results

Inhibition of FITC-labeled AAC uptake by gp120—The gp120 is capable of binding to CXCR4 on HIV via CD4 [Ugolini (1997) J Immunol 159, 3000–3008; Staudinger (2001) Biochem. Biophys. Res. Commun. 280, 1003–1007]. As shown in FIGS. 13a–b, co-incubation of PM1 cells with gp120 and the fluorescently labeled NeoR6 and R3G, significantly reduced the uptake of the AACs, while it did not essentially inhibit the uptake of ParomR5-FITC or NeamR4-FITC (not shown). Thus the presence of 5 μM HIV-1$_{IIIB}$ gp120 reduced the uptake of 0.5 PM NeoR6-FITC or R3G-FITC by ~40%, from MFI of 92 to 60, and from 74 to 49 (with a MFI background of 10) for NeoR6-FITC and R3G-FITC, respectively (FIGS. 13a–b).

Example 9

Development of HIV-Iresistant Isolates to NeoR6 in Cell Culture

Materials and Experimental Procedures

NeoR6 and R3G were synthesized and purified as detailed before [Litovchick (2000), Supra; Litovchick (1991) Supra; Litovchick (2001) Supra]. NeoR6 and R3G were dissolved in H$_2$O before use. Dideoxycytosine (ddC) and the HIV1$_{IIIB}$ laboratory strain of HIV-1 were obtained through the AIDS Research and Reference Reagent Program, Division of AIDS, NIAID, NIH. SDF-1α was obtained from PeproTech Inc. Rocky Hill, N.J. The CD4+ MT-2 cell line was obtained from the American Type Culture Collection. The cMAGI cells were a generous gift from Dr. Phalguni Gupta, University of Pittsburgh, Pittsburgh, USA.

Cell culture and inhibition of HIV-1 infection—MT2 cells were cultured in RPMI 1640, containing 10% fetal calf serum (FCS) and antibiotics. cMAGI HIV-1 reporter cells were cultured in 90% DMEM medium containing 10% FCS, 0.2 mg/ml geneticin (G418) and 0.1 μg/ml puromycin. The cMAGI assay is based on the ability of HIV-1 TAT to transactivate the expression of an integrated β-galactosidase reporter gene driven by the HIV-LTR [Chackerian, B. et al., 1997. J Virol. 71: 3932–3939; Collins, K. B. et al., 2000. Nat. Med. 6: 475–479]. The β-galactosidase reporter has been modified to remain localized in the nucleus where it can be detected with the X-gal substrate as an intense nuclear stain within a few days of infection. The X-gal substrate used was 5-bromo-4-chloro-3-indoyl-beta-D-galactopyranoside. HIV1$_{IIIB}$ was propagated by subculture in MT2 as described previously [Litovchick (2001) Supra].

Aliquots of cell-free culture supernatants were used as viral inoculum. The effective concentration which causes 50 percent inhibition (EC$_{50}$) of NeoR6 or other drugs was determined by incubating MT2 or cMAGI HIV-1 reporter cells with 0.2–0.5 multiplicity of infection of HIV-1$_{IIIB}$ wild type (wt) or resistant virus for 3–5 days at 37° C. in the presence or absence of various concentrations of NeoR6. The cytopathic effects of the viral infection of MT2 cells were analyzed by microscopic assessment of syncytium formation. These latter data were obtained by analysis of duplicate samples by two independent observers. HIV-1 infection of cMAGI cells was determined by counting the number of HIV-1 infected cells (stained blue).

Selection of NeoR6 HIV-1 resistant isolates—MT2 cells (3×10⁵ cells in 1 ml) were preincubated for 30 min with 1.9 μM of NeoR6 (the EC$_{50}$ value) and then infected with HIV-1$_{IIIB}$ (5×10⁵ TCID$_{50}$). Culture fluids were replaced device weekly with fresh medium containing an appropriate drug concentration. During the propagation of the virus, when at each cycle (at certain NeoR6 concentration) about 70% syncytium appeared, 250 μl of undiluted clarified culture supernatant, obtained from the HIV-infected cells, were added to 3×10⁵ fresh MT2 cells in 1 ml final volume, containing 2 times higher NeoR6 concentration. From the final cycle of each experiment the resistant virus was propagated as described above. The EC$_{50}$ of the AACs against the resistant NeoR6 isolates was examined and compared to the wt virus. After 24 to 26 cycles of selection of NeoR6 HIV-1 resistant isolates, genomic DNA was purified from the infected MT2 cells according to Sambrook et al (Sambrook et al., 1989).

Experimental Results

Selection of NeoR6$^{RES}$ isolates—Three sets of selection for NeoR6 resistant HIV-1 isolates were carried out by gradually increasing the concentration of NeoR6 in culture from 1.9 μM (~EC$_{50}$) to 150 μM. The increase in NeoR6 concentration was effected for 7–9 weeks, and then the virus was further grown for additional 4 weeks at 150 μM. It will be appreciated that the concentration of NeoR6 could not have been increased since cell toxicity was observed above this concentration. At the end of the 11–13 weeks of selection for NeoR6 resistant isolates, the sensitivity of the three NeoR6 isolates to NeoR6, R3G, SDF-1α (the natural ligand of CXCR4) and ddC (a nucleoside analog) was determined. As is shown in Table 4, hereinbelow, following 25 passages, the NeoR6 resistant isolates were ~46 times more resistant than the wild type (wt) virus to NeoR6, i.e. the EC$_{50}$ to NeoR6 increased from 1.9±0.96 to 87±34 μM. The NeoR6 resistant isolates were also ~5 times more resistant to R3G (EC$_{50}$ increased from 4.1±2.4 μM for the wt virus to 21±8.8 μM for the NeoR6 resistant isolates). In contrast, the NeoR6 resistant isolates were not resistant to SDF-1α (EC$_{50}$=1 μg/ml for both wt and NeorR6 resistant HIV-1 isolates, Table 4, hereinbelow). The resistance phenotype was maintained even in the absence of inhibitor for 1 month (data not shown). Resistant isolated exhibited a replication rate similar to that of wt HIV-1$_{IIIB}$ virus (data not shown).

TABLE 4

Inhibition of HIV-1$_{IIIB}$ wt and
NeoR6 resistant isolates by antivirals

| Antiviral | Wild-type | NeoR6$^{RES}$ |
|---|---|---|
| NeoR6 | 1.9 ± 0.96 | 87 ± 34 |
| R3G | 4.1 ± 2.4 | 21 ± 8.8 |

TABLE 4-continued

Inhibition of HIV-1$_{IIIB}$ wt and
NeoR6 resistant isolates by antivirals

| Antiviral | Wild-type | NeoR6$^{RES}$ |
|---|---|---|
| SDF-1α | 0.2 ± 0.05 | 0.18 ± 0.07 |
| ddC | 0.3 ± 0.1 | 0.3 ± 0.13 |

The numbers represent the mean and standard deviation values of EC$_{50}$ (μM) of three separate experiments.

Since as is illustrated herein NeoR6 resistant isolates were obtained only at NeoR6 concentrations which are far above the concentrations anticipated to be used in treating a viral infection (e.g., HIV), the AAC of the present invention represent efficient and safe antiviral agents.

Example 10

Mutations in GP120 and GP41 in NeoR6$^{RES}$ Isolates

Background

The present inventors have previously found that AACs bind in vitro with high affinity to TAR and RRE RNA [Litovchick, A. et al., 1999. FEBS Lett. 445: 73–79; Carriere, M. et al., 2002. RNA. 8: 1267–1279; Litovchick et al., 2000 (Supra)]. In addition, it was hypothesized that the AACs may also bind to other intracellular factors [Litovchick, A. et al., 2001. Biochemistry 40: 15612–15623; Borkow, G. et al., 2003. Antiviral Res. 60: 181–92; Borkow, G. et al., 2003, Biochemical and Biophysical Research Communications, 312: 1047–1052), such as with HIV-1 dimerization initiation site (DIS), as was recently demonstrated for aminoglycosides (Ennifar, E. et al., 2003. J. Biol. Chem. 278: 2723–2730). In order to identify mutations that affect AAC binding, the genome of the NeoR6res HIV-1 isolates was subjected to sequence analysis, as follows.

Materials and Experimental Procedures

Sequencing of genomic regions of the NeoR6$^{res}$ HIV-1 isolates—PCR amplification of several genomic regions was carried out using Taq DNA polymerase (Sigma, Rehovot, Israel) and specific forward and reverse primers (all synthesized at the Biological services, Weizmann Institute of Science) as listed in Table 5, hereinbelow. Amplified products were purified by gel electrophoresis on 2% agarose gels. Sequencing of several areas of the genome isolated both from the NeoR6$^{res}$ HIV-1 isolates and from the three HIV-1$_{IIIB}$ aliquots used at the beginning of each set of NeoR6 resistance selection was carried out using the forward primer on the ABI Prism, 3700 DNA Analyzer, PE, Applied Biosystems, HITACHI.

TABLE 5

Primers used to amplify and sequence genes of NeoR6 resistant isolates.

| Gene Area Sequenced | Location in Genome | Fragment Amplified | Forward Primer (5'→3') | Reverse Primer (5'→3') |
|---|---|---|---|---|
| TAR | 1–57 | 1–220 | ttctcgcttgtactgggtctc (SEQ ID NO: 1) | cgttttcaagtccctgttcg (SEQ ID NO: 2) |
| DIS | 245–290 | 178–431 | tggaaaatctctagcagtggc (SEQ ID NO: 3) | tttttctttccccctgg (SEQ ID NO: 4) |
| Tat$_{(1)}$ | 5377–5591 | 5334–5784 | cgacatagcagaataggcgtt (SEQ ID NO: 5) | tccttcactctcattgccact (SEQ ID NO: 6) |
| Rev$_{(1)}$ | 5516–5591 | 5462–5846 | agtgttgctttcattgccaag (SEQ ID NO: 7) | tcaacatcccaaggagcat (SEQ ID NO: 8) |
| gp120 | 5855–7303 | 6549–7214 | tgttaaatggcagcctagca (SEQ ID NO: 9) | cacttctccaattgtccctca (SEQ ID NO: 10) |
| gp41 | 7304–8338 | 7424–8350 | cagaacaatttgctgagggcta (SEQ ID NO: 11) | ccacccatcttatagcaaaatcc (SEQ ID NO: 12) |
| RRE | 7325–7530 | 7293–7568 | gagaaaaagagcagtgggaa (SEQ ID NO: 13) | cagagcaaccttaaatcccaa (SEQ ID NO: 14) |
| Tat$_{(2)}$ | 7925–7970 | 7895–8094 | aggcagggatattcaccatt (SEQ ID NO: 15) | agtaagtctctcaagcggtgg (SEQ ID NO: 16) |
| Rev$_{(2)}$ | 7925–8199 | 7910–8324 | ccattatcgtttcagaccca (SEQ ID NO: 17) | ccaagccctgtcttattcttc (SEQ ID NO: 18) |

The numbers correspond to the genomic sequence of HIV-1 (GenBank Accession No. NC_001802). The PCR primers were designed according to this particular isolate.

Experimental Results

Lack of mutations in the TAR RNA, DIS, RRE, Tat and Rev genomic sequences in NeoR6$^{res}$ HIV-1 isolates—Sequence comparison between wild-type (wt) HIV-1 and NeoR6$^{res}$ viruses revealed no differences (i.e., lack of mutations) in the TAR RNA, the dimerization initiation site (DIS), the Rev Response Element (RRE), the Tat or Rev genes.

Identification of mutations in the Env proteins of the NeoR6$^{res}$ HIV-1 isolates—As is shown in FIG. 14 and in Table 6, hereinbelow, several mutations were found in the genomic sequence of the Env proteins of NeoR6$^{res}$ HIV-1 isolates. Three missense mutations were found in the surface glycoprotein gp120 gene of the NeoR6 resistant isolates: I339T in the C3 region, S372L in the V4 region, and Q395K in the C4 region. In addition, as is further shown in Table 6, hereinbelow, two mutations were found in the transmembrane glycoprotein gp41 gene: S668R and F672Y in the 'heptad repeat' 2 (HR2).

The mutations in the gp120 gene of the NeoR6 resistant HIV-1 isolates did not appear at the V3 loop of gp120, as was found for other HIV-1 inhibitors of gp120-CXCR4 interaction (de Vreese, K. et al., 1996. J. Virol. 70: 689–696; Schols, D. et al., 1998. J Virol. 72: 4032–4037), but rather at the constant regions C3 and C4, and in the variable region V4. Although the V3 domain of gp120 was found to be necessary for interaction with the HIV-1 chemokine coreceptors, other domains of gp120 were also found to play a role in the interaction of gp120 with CCR5 (Wu, L. et al., 1996. Nature 384: 179–183; Trkola, A. et al., 1996. Nature 384: 184–187). The role of the V3 domain in the interaction of gp120 with CXCR4 has not been directly demonstrated; variable domains such as V1/V2 and V3 of gp120 can both contribute to the interaction with CXCR4 coreceptor (Mondor, I. et al., 1998. Virology 248: 394–405). Therefore, it can not be excluded that the mutations that were found by the present inventors in the NeoR6 resistant isolates confer resistance by allowing the interaction of gp120 with CXCR4 in such a way that NeoR6 interference would be minimized.

TABLE 6

Mutations in NeoR6$^{res}$ virus

| Gene | Amino acid position in gp160 precursor | Amino acid position within mature protein | Region in gene | Wild-type virus Codon | Wild-type virus Amino acid | NeoR6$^{res}$ virus Codon | NeoR6$^{res}$ virus Amino acid |
|---|---|---|---|---|---|---|---|
| gp120 | 371 | 343 | C3 | ATT | I | ACT | T |
| gp120 | 405 | 377 | V4 | TCA | S | TTA | L |
| gp120 | 428 | 400 | C4 | CAG | Q | AAG | K |
| gp41 | 668 | 157 | HR2 | AGT | S | AGA | R |
| gp41 | 673 | 162 | HR2 | TTT | F | TAT | Y |

The amino acid positions of the mutations are indicated within the gp160 precursor protein (GenBank Accession No: NP_057856) and the gp120 (GenBank Accession No: NP_579894) or gp41 (GenBank Accession No: NP_579895).

Analysis and Discussion

The identification of mutations in the Env genes of the HIV-1 genome of NeoR6$^{res}$ HIV-1 isolates [Borkow, G., et al., 2003. (Supra)] is in accordance with the notion that the main mode of action of the AACs is the interference with the initial steps of HIV-1 entry into the cells [Lapidot, A. and Litovchick, A. 2001. Drug Development Research 50: 502–515; Litovchick, (2001) Supra; Borkow (2003) Supra; Cabrera, C. et al., 2000. AIDS Res. Hum. Retroviruses 16: 627–634; Cabrera, C. et al., 2002. Antiviral Res. 53: 1–8; Catani, M. V. (2003) J Neurochem. 84: 1237–45].

It is now agreed that the binding of the CCR5 or CXCR4 coreceptors is made possible by the conformational changes induced in gp120 by CD4 binding; the resulting structural rearrangements of gp120 domains create the coreceptor-binding site (Rizzuto, C. D. et al., 1998. Science 280: 1949–1953). Together, CD4 and the coreceptor binding induce additional conformational changes in gp41. As a result of this transition, the fusion peptide and transmembrane domain of gp41, along with their associated membranes, are brought into close proximity (Weissenhorn, W. et al., 1997. Nature 387: 426–430; Chan, D. C. et al., D. 1997. Cell 89: 263–273).

The identification of mutations in the gp120 and gp41 genes strongly suggest that NeoR6 obstruct HIV-1 infection by interfering with the fusion step, dependent of both conformational changes in gp120 following CD4 and CXCR4 interaction, as well as by conformational changes in gp41 induced by HR1 and HR2 interaction. One mutation in the gp 120 C4 region associated with a change of nonpolar (Q) to polar (K) amino acid residues. Similarly two positions in the HR2 of gp41 are associated with changes of nonpolar (S and F) to polar (R and Y) amino acid residues, which apparently accounted for their sensitivity or resistance to NeoR6. Nonpolar residues in this region therefore appear to be important for the antiviral activity of NeoR6.

The lack of mutation in the V3 loop of gp120 in the NeoR6$^{res}$ isolates may be due to the conformational changes induced by NeoR6 during binding to the coreceptor CXCR4, with the conserved arginine groups of the V3 loop of gp120.

In conclusion, the AAC compounds of the present invention, and in particularly, NeoR6, may represent a new class of fusion inhibitors of HIV-1 replication.

Example 11

Antimicrobial Effect of the AAC of the Present Invention

Material and Experimental Methods

Evaluation of antimicrobial effects of NeoR6—The minimal inhibitory concentration of NeoR6 was determined using conventional clinical microbiology techniques. NeoR6 was diluted using serial two-fold dilutions (200 μg/ml down to 0.39 μg/ml) in TSB (ABBREVIATIONS?) liquid media for all microorganisms.

Experimental Results

Antimicrobial effect of NeoR6—The minimal inhibitory concentration (MIC) of NeoR6 was determined in a series of Gram-negative or Gram-positive bacteria. As is shown in Table 7, hereinbelow, most Gram-positive bacteria (e.g., *S. epidermidis, B. subtilis* and *S. aureus*) were relatively susceptible to the NeoR6, with an 8-fold variation in range. The Gram-negative were generally less susceptible, though all were inhibited by 100 mg/L of NeoR6.

TABLE 7

MIC values of NeoR6

| Bacteria | MIC (mg/L) |
|---|---|
| S. epidermidis | 0.78 |
| B. subtilis | 1.56 |
| S. aureus | 6.25 |
| P. aeruginosa; E. coli; | 100 |
| E. faecalisr | ≧200 |

Thus, NeoR6 is capable of inhibiting the growth of a variety of Gram-positive bacteria. These results therefore demonstrate the antibacterial effect of the AAC of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A pentaargininamido-paromomycin conjugate.

2. An argininamido-paramomycin conjugate of the formula:

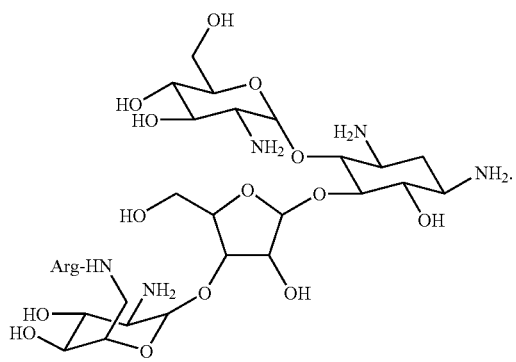

3. A tetraargininamido-neamine conjugate.

4. A argininamido-neomycin B conjugate of the formula:

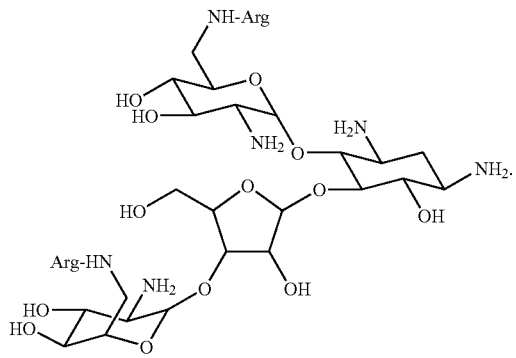

5. An argininamido-neomycin B conjugate of the formula:

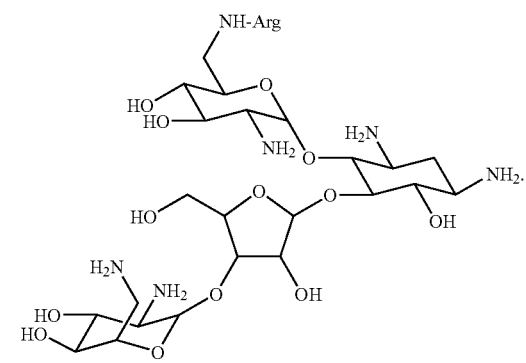

6. An argininamido-neomycin B conjugate of the formula:

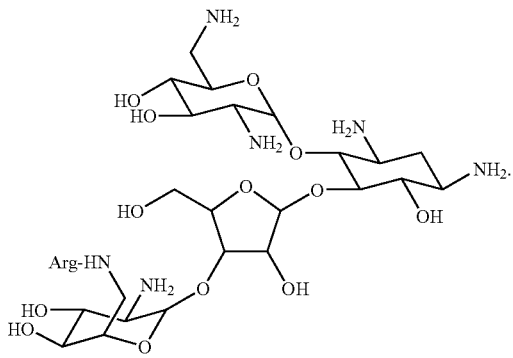

* * * * *